US006953669B2

(12) United States Patent
Dai

(10) Patent No.: US 6,953,669 B2
(45) Date of Patent: Oct. 11, 2005

(54) HUMAN GAK-RELATED GENE VARIANTS ASSOCIATED WITH LUNG CANCER

(76) Inventor: Ken-Shwo Dai, 1F., No. 18, Industry E. Rd., IV, Science-Based Industrial Park, Hsinchu (TW)

( * ) Notice: Subject to any disclaimer, the term of this patent is extended or adjusted under 35 U.S.C. 154(b) by 491 days.

(21) Appl. No.: 10/102,549

(22) Filed: Mar. 20, 2002

(65) Prior Publication Data

US 2003/0190736 A1 Oct. 9, 2003

(51) Int. Cl.[7] .......................... C12N 9/12; G01N 33/53; G01N 33/574; A61K 38/00; C07K 1/00

(52) U.S. Cl. ........................ 435/7.4; 194/7.23; 194/7.1; 194/15; 530/300; 530/350

(58) Field of Search ........................... 435/194, 7.1, 15, 435/7.4, 7.23; 530/300, 350

(56) References Cited

FOREIGN PATENT DOCUMENTS

WO WO2003033680 * 4/2003

OTHER PUBLICATIONS

"On the preparation and utilization of isolated and purified oligonucleotides" [electronic resource], Andrew Chin, allegedly deposited in UNC library on Mar. 14, 2002, date of publication, if any, is in question.
Sethi, T. "Science, medicine, and the future: Lung cancer" *BMJ*, 314 (7081): 652, (1997).
Kanaoka, Y., et al. "GAK: a cyclin G associated kinase contains a tensin/auxilin–like domain" *FEBS Letters*, vol. 402, pp. 73–80, (1997).
Reimer, C.L., et al. "Altered Regulation of Cyclin G in Human Breast Cancer and Its Specific Localization at Replication Foci . . . Cells" *J. of Bio. Chem.*, vol. 274, No. 16, pp. 11022–11029, (1999).
Keyomarsi, K., et al. "Redundant cyclin overexpression and gene amplification in breast cancer cells" *Proc. Natl. Acad. Sci. USA*, vol. 90, pp. 1112–1116, (1993).
Horne, M.C., et al. "Cyclin G1 and Cyclin G2 Comprise a New Family of Cyclins with Contrasting Tissue–specific and Cell . . . Expression" *J. of Bio. Chem.*, vol. 271, No. 11, pp. 6050–6061, (1996).
Kimura, S.H., et al. "Structure, Expression, and Chromosomal Localization of Human GAK" *Genomics*, vol. 44, pp. 179–187, (1997).
Michelland, S., et al. "Comparison of Chromosomal Imbalances in Neuroendocrine and Non–Small–Cell Lung Carcinomas" *Cancer Genet Cytogenet*, vol. 114, pp. 22–30, (1999).

* cited by examiner

*Primary Examiner*—Rebecca E. Prouty
*Assistant Examiner*—Malgorzata A. Walicka
(74) *Attorney, Agent, or Firm*—Ladas and Parry LLP

(57) ABSTRACT

The invention relates to the nucleic acid and polypeptide sequences of two novel human GAK-related gene variants.

The invention also relates to the process for producing the polypeptides of the variants.

The invention further relates to the use of the nucleic acid and polypeptide sequences of the gene variants in diagnosing diseases associated with the deficiency of GAK gene, in particular, iron homeostasis impairment-related diseases or non-small cell lung cancer (NSCLC), e.g. large cell lung cancer.

6 Claims, 29 Drawing Sheets

FIG. 1A

```
AGCCACCGCCATGTCGCTGCTGCAGTCTGCGCTCGACTTCTTGGCGGGTCCAGGCTCCCT - 60
          M  S  L  L  Q  S  A  L  D  F  L  A  G  P  G  S  L   -17
GGGCGGTGCTTCCGGCCGCGACCAGAGTGACTTCGTGGGCAGACGGTGGAACTGGGCGA - 120
 G  G  A  S  G  R  D  Q  S  D  F  V  G  Q  T  V  E  L  G  E   -37
GCTGCGGCTGCGGGTGCGGCGGGTCCTGGCCGAAGGAGGGTTTGCATTTGTGTATGAAGC - 180
 L  R  L  R  V  R  R  V  L  A  E  G  G  F  A  F  V  Y  E  A   -57
TCAAGATGTGGGGAGTGGCAGAGAGTATGCATTAAAGAGGCTATTATCCAATGAAGAGGA - 240
 Q  D  V  G  S  G  R  E  Y  A  L  K  R  L  L  S  N  E  E  E   -77
AAAGAACAGAGCCATCATTCAAGAAGTTTGCTTCATGAAAAAGCTTTCCGGCCACCCGAA - 300
 K  N  R  A  I  I  Q  E  V  C  F  M  K  K  L  S  G  H  P  N   -97
CATTGTCCAGTTTTGTTCTGCAGCCTCTATAGGAAAAGAGGAGTCAGACACGGGGCAGGC - 360
 I  V  Q  F  C  S  A  A  S  I  G  K  E  E  S  D  T  G  Q  A  -117
TGAGTTCCTCTTGCTCACAGAGCTCTGTAAAGGGCAGCTGGTGGAATTTTTGAAGAAAAT - 420
 E  F  L  L  L  T  E  L  C  K  G  Q  L  V  E  F  L  K  K  M  -137
GGAATCTCGAGGCCCCCTTTCGTGCGACACGGTTCTGAAGATCTTCTACCAGACGTGCCG - 480
 E  S  R  G  P  L  S  C  D  T  V  L  K  I  F  Y  Q  T  C  R  -157
CGCCGTGCAGCACATGCACCGGCAGAAGCCGCCCATCATCCACAGGGACCTCAAGGTTGA - 540
 A  V  Q  H  M  H  R  Q  K  P  P  I  I  H  R  D  L  K  V  E  -177
GAACTTGTTGCTTAGTAACCAAGGGACCATTAAGCTGTGTGACTTTGGCAGTGCCACGAC - 600
 N  L  L  L  S  N  Q  G  T  I  K  L  C  D  F  G  S  A  T  T  -197
CATCTCGCACTACCCTGACTACAGCTGGAGCGCCCAGAGGCGAGCCCTGGTGGAGGAAGA - 660
 I  S  H  Y  P  D  Y  S  W  S  A  Q  R  R  A  L  V  E  E  E  -217
```

FIG. 1B

```
GATCACGAGGAATACAACACCAATGTATAGAACACCAGAAATCATAGACTTGTATTCCAA - 720
 I  T  R  N  T  T  P  M  Y  R  T  P  E  I  I  D  L  Y  S  N   -237
CTTCCCGATCGGCGAGAAGCAGGATATCTGGGCCCTGGGCTGCATCTTGTACCTGCTGTG - 780
 F  P  I  G  E  K  Q  D  I  W  A  L  G  C  I  L  Y  L  L  C   -257
CTTCCGGCAGCACCCTTTTGAGGATGGAGCGAAACTTCGAATAGTCAATGGGAAGTACTC - 840
 F  R  Q  H  P  F  E  D  G  A  K  L  R  I  V  N  G  K  Y  S   -277
GATCCCCCCGCACGACACGCAGTACACGGTCTTCCACAGCCTCATCCGCGCCATGCTGCA - 900
 I  P  P  H  D  T  Q  Y  T  V  F  H  S  L  I  R  A  M  L  Q   -297
GGTGAACCCGGAGGAGCGGCTGTCCATCGCCGAGGTGGTGCACCAGCTGCAGGAGATCGC - 960
 V  N  P  E  E  R  L  S  I  A  E  V  V  H  Q  L  Q  E  I  A   -317
GGCCGCCCGCAACGTGAACCCCAAGTCTCCCATCACACAGCTCCTGGACCACAATGGAGG   1020
 A  A  R  H  V  N  P  K  S  P  I  T  E  L  L  E  Q  N  G  G   -337
CTACGGGAGCGCCACACTGTCCCGAGGGCCACCCCCTCCCGTGGCCCCGCTGGCAGTGG - 1080
 Y  G  S  A  T  L  S  R  G  P  P  P  P  V  G  P  A  G  S  G   -357
CTACAGTGGAGGCCTGGCGCTGGCGGAGTACGACCAGCCGTATGGCGGCTTCCTGGACAT - 1140
 Y  S  G  G  L  A  L  A  E  Y  D  Q  P  Y  G  G  F  L  D  I   -377
TCTGCGGGGTGGGACAGAGCGGCTCTTCACCAACCTCAAGGACACCTCCTCCAAGGTCAT - 1200
 L  R  G  G  T  E  R  L  F  T  N  L  K  D  T  S  S  K  V  I   -397
CCAGTCCGTCGCTAATTATGCAAAGGGTGACCTGGACATATCTTACATCACATCCAGAAT - 1260
 Q  S  V  A  N  Y  A  K  G  D  L  D  I  S  Y  I  T  S  R  I   -417
TGCAGTGATGTCATTCCCAGCAGAAGGTGTGGAGTCAGCGCTCAAAAACAACATCGAAGA - 1320
 A  V  M  S  F  P  A  E  G  V  E  S  A  L  K  N  N  I  E  D   -437
```

FIG. 1C

```
TGTGCGGTTGTTCCTGGACTCCAAGCACCCAGGGCACTATGCCGTCTACAACCTGTCCCC - 1380
 V  R  L  F  L  D  S  K  H  P  G  H  Y  A  V  Y  N  L  S  P   -457
GAGGACCTACCGGCCCTCCAGGTTCCACAACCGGGTCTCCGAGTGTGGCTGGGCAGCACG - 1440
 R  T  Y  R  P  S  R  F  H  N  R  V  S  E  C  G  W  A  A  R   -477
GCGGGCCCCACACCTGCACACCCTGTACAACATCTGCAGGAACATGCACGCCTGGCTGCG - 1500
 R  A  P  H  L  H  T  L  Y  N  I  C  R  N  M  H  A  W  L  R   -497
GCAGGACCACAAGAACGTCTGCGTCGTGCACTGCATGGACGGAGAGCCGCGTCTGCTGT - 1560
 Q  D  H  K  N  V  C  V  V  H  C  M  D  G  R  A  A  S  A  V   -517
GGCCGTCTGCTCCTTCCTGTGCTTCTGCCGTCTCTTCAGCACCGCGGAGGCCGCCGTGTA - 1620
 A  V  C  S  F  L  C  F  C  R  L  F  S  T  A  E  A  A  V  Y   -537
CATGTTCAGCATGAAGCGCTGCCCACCAGGCATCTGGCCATCCCACAAAAGGTACATCGA - 1680
 M  F  S  M  K  R  C  P  P  G  I  W  P  S  H  K  R  Y  I  E   -557
GTACATCTGTCACATGGTCGCGGAGGAGCCCATCACACCCCACAGCAAGCCCATCCTGGT - 1740
 Y  M  C  D  M  V  A  E  E  P  I  T  P  H  S  K  P  I  L  V   -577
GAGGGCCGTGGTCATGACACCCGTGCCGCTGTTCAGCAAGCAGAGGAGCGGCTGCAGGCC - 1800
 R  A  V  V  M  T  P  V  P  L  F  S  K  Q  R  S  G  C  R  P   -597
CTTCTGCGAGGTCTACGTGGGGGACGAGCGTGTGGCCAGCACCTCCCAGGAGTACGACAA - 1860
 F  C  E  V  Y  V  G  D  E  R  V  A  S  T  S  Q  E  Y  D  K   -617
GATGCGGGACTTTAAGATTGAAGATGGCAAAGCGGTGATTCCCCTGGGCGTCACGGTGCA - 1920
 M  R  D  F  K  I  E  D  G  K  A  V  I  P  L  G  V  T  V  Q   -637
AGGAGACGTGCTCATCGTCATCTATCACGCCCGGTCCACTCTGGGCGGCCGGCTGCAGGC - 1980
 G  D  V  L  I  V  I  Y  H  A  R  S  T  L  G  G  R  L  Q  A   -657
CAAGATGGCATCCATGAAGATGTTCCAGATTCAGTTCCACACGGGGTTTGTGCCTCGGAA - 2040
 K  M  A  S  M  K  M  F  Q  I  Q  F  H  T  G  F  V  P  R  N   -677
```

FIG. 1D

```
CGCCACCACTGTGAAATTTGCCAAGTATGACCTGGACGCGTGTGACATTCAAGAAAAATA - 2100
 A  T  T  V  K  F  A  K  Y  D  L  D  A  C  D  I  Q  E  K  Y   -697
CCCGGATTTATTTCAAGTGAACCTGGAAGTGGAGGTGGAGCCCAGGGACAGGCCGAGCCG - 2160
 P  D  L  F  Q  V  N  L  E  V  E  V  E  P  R  D  R  P  S  R   -717
GGAAGCCCCACCATGGGAGAACTCGAGCATGAGGGGGCTGAACCCCAAAATCCTGTTTTC - 2220
 E  A  P  P  W  E  N  S  S  M  R  G  L  N  P  K  I  L  F  S   -737
CAGCCGGGAGGAGCAGCAAGACATTCTGTCTAAGTTTGGGAAGCCGGAGCTTCCCCGGCA - 2280
 S  R  E  E  Q  Q  D  I  L  S  K  F  G  K  P  E  L  P  R  Q   -757
GCCTGGCTCCACGGCTCAGTATGATGCTGGGGCAGGGTCCCCGGAAGCCGAACCCACAGA - 2340
 P  G  S  T  A  Q  Y  D  A  G  A  G  S  P  E  A  E  P  T  D   -777
CTCTGACTCACCGCCAAGCAGCAGCGCGGACGCCAGTCGCTTCCTGCACACGCTGGACTG - 2400
 S  D  S  P  P  S  S  S  A  D  A  S  R  F  L  H  T  L  D  W   -797
GCAGGAAGAGAAGGAGGCAGAGACTGGTGCAGAAAATGCCTCTTCCAAGCAGAGCGAGTC - 2460
 Q  E  E  K  E  A  E  T  G  A  E  N  A  S  S  K  E  S  E  S   -817
TGCCCTGATGGAGGACAGAGACGAGAGTGAGGTGTCAGATGAAGGGGGATCCCCGATCTC - 2520
 A  L  M  E  D  R  D  E  S  E  V  S  D  E  G  G  S  P  I  S   -837
CAGCGAGGGCCAGGAACCCAGGGCCGACCCAGAGCCCCCCGGCCTGGCAGCAGGGCTGGT - 2580
 S  E  G  Q  E  P  R  A  D  P  E  P  P  G  L  A  A  G  L  V   -857
GCAGCAGGACTTGGTTTTTGAGGTGGAGACACCGGCTGTGCTGCCAGAGCCTGTGCCACA - 2640
 Q  Q  D  L  V  F  E  V  E  T  P  A  V  L  P  E  P  V  P  Q   -877
GGAAGACGGGGTCGACCTCCTGGGCCTGCACTCCGAGGTGGGCGCAGGGCCAGCTGTACC - 2700
 E  D  G  V  D  L  L  G  L  H  S  E  V  G  A  G  P  A  V  P   -897
CCCGCAGGCCTGCAAGGCCCCCTCCAGCAACACCGACCTGCTCAGCTGCCTCCTTGGCC  - 2760
 P  Q  A  C  K  A  P  S  S  N  T  D  L  L  S  C  L  L  G  P   -917
```

FIG. 1E

```
CCCTGAGGCCGCCTCCCAGGGGCCCCCGGAGGATCTGCTCAGCGAGGACCCGCTGCTCCT - 2820
 P  E  A  A  S  Q  G  P  P  E  D  L  L  S  E  D  P  L  L  L   -937
GGCAAGCCCGGCCCCTCCCCTGAGCGTGCAGAGCACCCCAAGAGGAGGGCCCCCTGCCGC - 2880
 A  S  P  A  P  P  L  S  V  Q  S  T  P  R  G  G  P  P  A  A   -957
TGGCAACAACTCCCAGCCCTGCTCCAATCCTGATCTCTTCGGCGAATTTCTCAATTCGGA - 2940
 G  N  N  S  Q  P  C  S  N  P  D  L  F  G  E  F  L  N  S  D   -977
CTCTGTGACCGTCCCACCATCCTTCCCGTCTGCCCACAGCGCTCCGCCCCCATCCTGCAG - 3000
 S  V  T  V  P  P  S  F  P  S  A  H  S  A  P  P  P  S  C  S   -997
CGCCGACTTCCTGCACCTGGGGGATCTGCCAGGAGAGCCCAGCAAGATGACAGCCTCGTC - 3060
 A  D  F  L  H  L  G  D  L  P  G  E  P  S  K  M  T  A  S  S  -1017
CAGCAACCCAGACCTGCTGGGAGGATGGCTGCCTGGACCGAGACTGCAGCGTCGGCAGT - 3120
 S  N  P  D  L  L  G  C  W  R  A  W  T  E  T  A  A  S  A  V  -1037
GGCCCCCACGCCAGCCACAGAAGGCCCCCTCTTCTCTCCTGGAGGTCAGCCGGCCCCTTG - 3180
 A  P  T  P  A  T  E  G  P  L  F  S  P  G  G  Q  P  A  P  C  -1057
TGGCTCTCAGGCCAGCTGGACCAAGTCTCAGAACCCGGACCCATTTGCTGACCTTGGCGA - 3240
 G  S  Q  A  S  W  T  K  S  Q  N  P  D  P  F  A  D  L  G  D  -1077
CCTCAGCTCCGGCCTCCAAGGCTCACCAGCTGGATTTCCTCCTGGGGGCTTCATTCCCAA - 3300
 L  S  S  G  L  Q  G  S  P  A  G  F  P  P  G  G  F  I  P  K  -1097
AACGGCCACCACGGCCAAAGGCAGCAGCTCCTGGCAGACAAGTCGGCCGCCAGCCCAGGG - 3360
 T  A  T  T  A  K  G  S  S  S  W  Q  T  S  R  P  P  A  Q  G  -1117
CGCCTCATGGCCCCCTCAGGCCAAGCCGCCCCCCAAAGCCTGCACACAGCCAAGGCCTAA - 3420
 A  S  W  P  P  Q  A  K  P  P  P  K  A  C  T  Q  P  R  P  N  -1137
CTATGCCTCGAACTTCAGTGTGATCGGGGCGCGGGAGGAGCGGGGGGTCCGCGCACCCAG - 3480
 Y  A  S  N  F  S  V  I  G  A  R  E  E  R  G  V  R  A  P  S  -1157
```

FIG. 1F

```
CTTTGCTCAAAAGCCAAAAGTCTCTGAGAACGACTTTGAAGATCTGTTGTCCAATCAAGG - 3540
 F  A  Q  K  P  K  V  S  E  N  D  F  E  D  L  L  S  N  Q  G  -1177
CTTCTCCTCCAGGTCTGACAAGAAAGGGCCAAAGACCATTGCAGAGATGAGGAAGCAGGA - 3600
 F  S  S  R  S  D  K  K  G  P  K  T  I  A  E  M  R  K  Q  D  -1197
CCTGGCTAAAGACACGGACCCACTCAAGCTGAAGCTCCTGGACTGGATTGAGGGCAAGGA - 3660
 L  A  K  D  T  D  P  L  K  L  K  L  L  D  W  I  E  G  K  E  -1217
GCGGAACATCCGGGCCCTGCTGTCCACGCTGCACACAGTGCTGTGGGACGGGGAGAGCCG - 3720
 R  N  I  R  A  L  L  S  T  L  H  T  V  L  W  D  G  E  S  R  -1237
CTGGACGCCCGTGGGCATGGCCGACCTGGTGGCTCCGGAGCAAGTGAAGAAGCACTATCG - 3780
 W  T  P  V  G  M  A  D  L  V  A  P  E  Q  V  K  K  H  Y  R  -1257
CCGCGCGGTGCTGGCCGTGCACCCCGACAAGGCTGCGGGGCAGCCGTACGAGCAGCACGC - 3840
 R  A  V  L  A  V  H  P  D  K  A  A  G  Q  P  Y  E  Q  H  A  -1277
CAAGATGATCTTCATGGAGCTGAATGACGCCTGGTCGGAGTTTGAGAACCAGGGCTCCCG - 3900
 K  M  I  F  M  E  L  N  D  A  W  S  E  F  E  N  Q  G  S  R  -1297
GCCCCTCTTCTGAGGCCGCAGTGGTGGTGGCTGCGCACACAGCTCCACAGGTTGGGAGCC - 3960
 P  L  F  *                                                   - 1300
GTCGTGGGACCTGGGTCCCCACCGTGAGGACCCCGTGGGCGACAGCAGGTGTGGCCAGGG - 4020
TGGGGCTCCGAGCCCCGGGTCACCGCCCGCCCAGCGTTCCAGGCACATGAAGAGAAAGCA - 4080
TTCCAAAGCCTCTGATTGTTGTTTCCTTTTTCTCCTCCCGAAGGAACAGCTGATTCATGC - 4140
TCCTCCCGCAATTGTCACGTCTGTGATTTATTTGGTGTTTCGGGCGTGGCCTCTGGAGCC - 4200
CCGGCACGTGGTGGCCACGCTGCTGGCGCTCATGGCCCTGGTGTTTGCACCGCACTTT - 4260
GTAATCAGTCCCGTGGTTGTCTGTACAGAATTAAACTATTTTCCGATG - 4308
```

FIG. 2A

```
GGCCGGCGGTTGCTGAGCTGACCCGGACGGCGAGGGAGCGGAGCCCGAGCCCGACCAC  - 60
TCCGGCTGCCGCGGGGTGCGGCGCAGCCACCGCCATGTCGCTGCTGCAGTCTGCGCTCGA - 120
                                    M  S  L  L  Q  S  A  L  D    -9
CTTCTTGGCGGGTCCAGGCTCCCTGGGCGGTGCTTCCGGCCGCGACCAGAGTGACTTCGT - 180
 F  L  A  G  P  G  S  L  G  G  A  S  G  R  D  Q  S  D  F  V   -29
GGGGCAGACGGTGGAACTGGGCGAGCTGCGGCTGCTCCTGGCAAGCCCGGCCCCTCCCCT - 240
 G  Q  T  V  E  L  G  E  L  R  L  L  L  A  S  P  A  P  P  L   -49
GAGCGTGCAGAGCACCCCAAGAGGAGGGCCCCCTGCCGCTGCTGACCCCTTTGGCCCGCT - 300
 S  V  Q  S  T  P  R  G  G  P  P  A  A  A  D  P  F  G  P  L   -69
TCTGCCGTCTTCAGGCAACAACTCCCAGCCCTGCTCCAATCCTGATCTCTTCGGCGAATT - 360
 L  P  S  S  G  N  N  S  Q  P  C  S  N  P  D  L  F  G  E  F   -89
TCTCAATTCGGACTCTGTGACCGTCCCACCATCCTTCCCGTCTGCCCACAGCGCTCCGCC - 420
 L  N  S  D  S  V  T  V  P  P  S  F  P  S  A  H  S  A  P  P  -109
CCCATCCTGCAGCGCCGACTTCCTGCACCTGGGGGATCTGCCAGGAGAGCCCAGCAAGAT - 480
 P  S  C  S  A  D  F  L  H  L  G  D  L  P  G  E  P  S  K  M  -129
GACAGCCTCGTCCAGCAACCCAGACCTGCTGGGAGGATGGGCTGCCTGGACCGAGACTGC - 540
 T  A  S  S  S  N  P  D  L  L  G  G  W  A  A  W  T  E  T  A  -149
AGCGTCGGCAGTGGCCCCCACGCCAGCCACAGAAGGCCCCCTCTTCTCTCCTGGAGGTCA - 600
 A  S  A  V  A  P  T  P  A  T  E  G  P  L  F  S  P  G  G  Q  -169
GCCGGCCCCTTGTGGCTCTCAGGCCAGCTGGACCAAGTCTCAGAACCCGGACCCATTTGC - 660
 P  A  P  C  G  S  Q  A  S  W  T  K  S  Q  N  P  D  P  F  A  -189
TGACCTTGGCGACCTCAGCTCCGGCCTCCAAGGCTCACCAGCTGGATTTCCTCCTGGGGG - 720
 D  L  G  D  L  S  S  G  L  Q  G  S  P  A  G  F  P  P  G  G  -209
```

FIG. 2B

```
CTTCATTCCCAAAACGGCCACCACGGCCAAAGGCAGCAGCTCCTGGCAGACAAGTCGGCC - 780
 F  I  P  K  T  A  T  T  A  K  G  S  S  S  W  Q  T  S  R  P   -229
GCCAGCCCAGGGCGCCTCATGGCCCCCTCAGGCCAAGCCGCCCCCAAAGCCTGCACACA - 840
 P  A  Q  G  A  S  W  P  P  Q  A  K  P  P  P  K  A  C  T  Q   -249
GCCAAGGCCTAACTATGCCTCGAACTTCAGTGTGATCGGGGCGCGGGAGGAGCGGGGGT - 900
 P  R  P  N  Y  A  S  N  F  S  V  I  G  A  R  E  E  R  G  V   -269
CCGCGCACCCAGCTTTGCTCAAAAGCCAAAAGTCTCTGAGAACGACTTTGAAGATCTGTT - 960
 R  A  P  S  F  A  Q  K  P  K  V  S  E  N  D  F  E  D  L  L   -289
GTCCAATCAAGGCTTCTCCTCCAGGTCTGACAAGAAAGGGCCAAAGACCATTGCAGAGAT - 1020
 S  N  Q  G  F  S  S  R  S  D  K  K  G  P  K  T  I  A  E  M   -309
GAGGAAGCAGGACCTGGCTAAAGACACGGACCCACTCAAGCTGAAGCTCCTGGACTGGAT - 1080
 R  K  Q  D  L  A  K  D  T  D  P  L  K  L  K  L  L  D  W  I   -329
TGAGGGCAAGCAGCGGAACATCCGGGCCCTGCTGTCCACGCTGCACACAGTGCTGTGGGA - 1140
 E  G  K  E  R  N  I  R  A  L  L  S  T  L  H  T  V  L  W  D   -349
CGGGGAGAGCCGCTGGACGCCCGTGGGCATGGCCGACCTGGTGGCTCCGGAGCAAGTGAA - 1200
 G  E  S  R  W  T  P  V  G  M  A  D  L  V  A  P  E  Q  V  K   -369
GAAGCACTATCGCCGCGCGGTGCTGGCCGTGCACCCCGACAAGGCTGCGGGGCAGCCGTA - 1260
 K  H  Y  R  R  A  V  L  A  V  H  P  D  K  A  A  G  Q  P  Y   -389
CGAGCAGCACGCCAAGATGATCTTCATGGAGCTGAATGACGCCTGGTCGGAGTTTGAGAA - 1320
 E  Q  H  A  K  M  I  F  M  E  L  N  D  A  W  S  E  F  E  N   -409
CCAGGGCTCCCGGCCCCTCTTCTGAGGCCGCAGTGGTGGTGGCTGCGCACACAGCTCCAC - 1380
 Q  G  S  R  P  L  F  *                                        - 416
```

FIG. 2C

```
AGGTTGGGAGCCGTCGTGGGACCTGGGTCCCCACCGTGAGGACCCCGTGGGCGACAGCAG - 1440
GTGTGGCCAGGGTGGGGCTCCGAGCCCCGGGTCACCGCCCGCCCAGCGTTCCAGGCACAT - 1500
GAAGAGAAAGCATTCCAAAGCCTCTGATTGTTGTTTCCTTTTTCTCCTCCCGAAGGAACA - 1560
GCTGATTCATGCTCCTCCCGCAATTGTCACGTCTGTGATTTATTTGGTGTTTCGGGCGTG - 1620
GCCTCTGGAGCCCCGGCACGTGGTGGCCACGCTGCTGGCGCTCATGGGCCCTGGTGTTT - 1680
GCACCGCACTTTGTAATCAGTCCCGTGGTTGTCTGTACAGAATTAAACTATTTTCCGATG - 1740
```

FIG. 3A

```
      1                                                         60
GAK2  ATGTCGCTGCTGCAGTCTGCGCTCGACTTCTTGGCGGGTCCAGGCTCCCTGGCGGTGCT
GAK1  ATGTCGCTGCTGCAGTCTGCGCTCGACTTCTTGGCGGGTCCAGGCTCCCTGGCGGTGCT
GAK   ATGTCGCTGCTGCAGTCTGCGCTCGACTTCTTGGCGGGTCCAGGCTCCCTGGCGGTGCT

      61                                                       120
GAK2  TCCGGCCGCGACCAGAGTGACTTCGTGGGGCAGACGGTGGAACTGGGCGAGCTGCGGCTG
GAK1  TCCGGCCGCGACCAGAGTGACTTCGTGGGGCAGACGGTGGAACTGGGCGAGCTGCGGCTG
GAK   TCCGGCCGCGACCAGAGTGACTTCGTGGGGCAGACGGTGGAACTGGGCGAGCTGCGGCTG

      121                                                      180
GAK2  C-----------------------------------------------------------
GAK1  CGGGTGCGGCGGGTCCTGGCCGAAGGAGGGTTTGCATTTGTGTATGAAGCTCAAGATGTG
GAK   CGGGTGCGGCGGGTCCTGGCCGAAGGAGGGTTTGCATTTGTGTATGAAGCTCAAGATGTG

      181                                                      240
GAK2  ------------------------------------------------------------
GAK1  GGGAGTGGCAGAGAGTATGCATTAAAGAGGCTATTATCCAATGAAGAGGAAAAGAACAGA
GAK   GGGAGTGGCAGAGAGTATGCATTAAAGAGGCTATTATCCAATGAAGAGGAAAAGAACAGA
```

FIG. 3 B

```
      241                                                        300
GAK2  ------------------------------------------------------------
GAK1  GCCATCATTCAAGAAGTTTGCTTCATGAAAAAGCTTTCCGGCCACCCGAACATTGTCCAG
GAK   GCCATCATTCAAGAAGTTTGCTTCATGAAAAAGCTTTCCGGCCACCCGAACATTGTCCAG

      301                                                        360
GAK2  ------------------------------------------------------------
GAK1  TTTTGTTCTGCAGCGTCTATAGGAAAAGAGGAGTCAGACACGGGGCAGGCTGAGTTCCTC
GAK   TTTTGTTCTGCAGCGTCTATAGGAAAAGAGGAGTCAGACACGGGGCAGGCTGAGTTCCTC

      361                                                        420
GAK2  ------------------------------------------------------------
GAK1  TTGCTCACAGAGCTCTGTAAAGGGCAGCTGGTGGAATTTTTGAAGAAAATGGAATCTCGA
GAK   TTGCTCACAGAGCTCTGTAAAGGGCAGCTGGTGGAATTTTTGAAGAAAATGGAATCTCGA

      421                                                        480
GAK2  ------------------------------------------------------------
GAK1  GGCCCCCTTTCGTGCGACACGGTTCTGAAGATCTTCTACCAGACGTGCCGCGCCGTGCAG
GAK   GGCCCCCTTTCGTGCGACACGGTTCTGAAGATCTTCTACCAGACGTGCCGCGCCGTGCAG

      481                                                        540
GAK2  ------------------------------------------------------------
GAK1  CACATGCACCGGCAGAAGCCGCCCATCATCCACAGGGACCTCAAGGTTGAGAACTTGTTG
GAK   CACATGCACCGGCAGAAGCCGCCCATCATCCACAGGGACCTCAAGGTTGAGAACTTGTTG
```

FIG. 3C

```
       541                                                         600
GAK2   ------------------------------------------------------------
GAK1   CTTAGTAACCAAGGGACCATTAAGCTGTGTGACTTTGGCAGTGCCACGACCATCTCGCAC
GAK    CTTAGTAACCAAGGGACCATTAAGCTGTGTGACTTTGGCAGTGCCACGACCATCTCGCAC

       601                                                         660
GAK2   ------------------------------------------------------------
GAK1   TACCCTGACTACAGCTGGAGCGCCCAGAGGCGAGCCCTGGTGGAGGAAGAGATCACGAGG
GAK    TACCCTGACTACAGCTGGAGCGCCCAGAGGCGAGCCCTGGTGGAGGAAGAGATCACGAGG

       661                                                         720
GAK2   ------------------------------------------------------------
GAK1   AATACAACACCAATGTATAGAACACCAGAAATCATAGACTTGTATTCCAACTTCCCGATC
GAK    AATACAACACCAATGTATAGAACACCAGAAATCATAGACTTGTATTCCAACTTCCCGATC

       721                                                         780
GAK2   ------------------------------------------------------------
GAK1   GGCGAGAAGCAGGATATCTGGGCCCTGGGCTGCATCTTGTACCTGCTGTGCTTCCGGCAG
GAK    GGCGAGAAGCAGGATATCTGGGCCCTGGGCTGCATCTTGTACCTGCTGTGCTTCCGGCAG

       781                                                         840
GAK2   ------------------------------------------------------------
GAK1   CACCCTTTTGAGGATGGAGCGAAACTTCGAATAGTCAATGGGAAGTACTCGATCCCCCCG
GAK    CACCCTTTTGAGGATGGAGCGAAACTTCGAATAGTCAATGGGAAGTACTCGATCCCCCCG
```

FIG. 3D

```
      841                                                         900
GAK2  ------------------------------------------------------------
GAK1  CACGACACGCAGTACACGGTCTTCCACAGCCTCATCCGCGCCATGCTGCAGGTGAACCCG
GAK   CACGACACGCAGTACACGGTCTTCCACAGCCTCATCCGCGCCATGCTGCAGGTGAACCCG

      901                                                         960
GAK2  ------------------------------------------------------------
GAK1  GAGGAGCGGCTGTCCATCGCCGAGGTGGTGCACCAGCTGCAGGAGATCGCGGCCGCCCGC
GAK   GAGGAGCGGCTGTCCATCGCCGAGGTGGTGCACCAGCTGCAGGAGATCGCGGCCGCCCGC

      961                                                        1020
GAK2  ------------------------------------------------------------
GAK1  AACGTGAACCCCAAGTCTCCCATCACAGAGCTCCTGGAGCAGAATGGAGGCTACGGGAGC
GAK   AACGTGAACCCCAAGTCTCCCATCACAGAGCTCCTGGAGCAGAATGGAGGCTACGGGAGC

      1021                                                       1080
GAK2  ------------------------------------------------------------
GAK1  GCCACACTGTCCCGAGGGCCACCCCCTCCCGTGGCCCCGCTGGCAGTGGCTACAGTGGA
GAK   GCCACACTGTCCCGAGGGCCACCCCCTCCCGTGGCCCCGCTGGCAGTGGCTACAGTGGA

      1081                                                       1140
GAK2  ------------------------------------------------------------
GAK1  GGCCTGGCGCTGGCGGAGTACGACCAGCCGTATGGCGGCTTCCTGGACATTCTGCGGGGT
GAK   GGCCTGGCGCTGGCGGAGTACGACCAGCCGTATGGCGGCTTCCTGGACATTCTGCGGGGT
```

FIG. 3E

```
     1141                                                      1200
GAK2 ------------------------------------------------------------
GAK1 GGGACAGAGCGGCTCTTCACCAACCTCAAGGACACCTCCTCCAAGGTCATCCAGTCCGTC
GAK  GGGACAGAGCGGCTCTTCACCAACCTCAAGGACACCTCCTCCAAGGTCATCCAGTCCGTC
     1201                                                      1260
GAK2 ------------------------------------------------------------
GAK1 GCTAATTATGCAAAGGGTGACCTGGACATATCTTACATCACATCCAGAATTGCAGTGATG
GAK  GCTAATTATGCAAAGGGTGACCTGGACATATCTTACATCACATCCAGAATTGCAGTGATG

     1261                                                      1320
GAK2 ------------------------------------------------------------
GAK1 TCATTCCCAGCAGAAGGTGTGGAGTCAGCGCTCAAAAACAACATCGAAGATGTGCGGTTG
GAK  TCATTCCCAGCAGAAGGTGTGGAGTCAGCGCTCAAAAACAACATCGAAGATGTGCGGTTG

     1321                                                      1380
GAK2 ------------------------------------------------------------
GAK1 TTCCTGGACTCCAAGCACCCAGGGCACTATGCCGTCTACAACCTGTCCCCGAGGACCTAC
GAK  TTCCTGGACTCCAAGCACCCAGGGCACTATGCCGTCTACAACCTGTCCCCGAGGACCTAC

     1381                                                      1440
GAK2 ------------------------------------------------------------
GAK1 CGGCCCTCCAGGTTCCACAACCGGGTCTCCGAGTGTGGCTGGGCAGCACGGCGGGCCCCA
GAK  CGGCCCTCCAGGTTCCACAACCGGGTCTCCGAGTGTGGCTGGGCAGCACGGCGGGCCCCA
```

FIG. 3F

```
       1441                                                      1500
GAK2   ------------------------------------------------------------
GAK1   CACCTGCACACCCTGTACAACATCTGCAGGAACATGCACGCCTGGCTGCGGCAGGACCAC
GAK    CACCTGCACACCCTGTACAACATCTGCAGGAACATGCACGCCTGGCTGCGGCAGGACCAC
       1501                                                      1560
GAK2   ------------------------------------------------------------
GAK1   AAGAACGTCTGCGTCGTGCACTGCATGGACGGGAGAGCCGCGTCTGCTGTGGCCGTCTGC
GAK    AAGAACGTCTGCGTCGTGCACTGCATGGACGGGAGAGCCGCGTCTGCTGTGGCCGTCTGC

       1561                                                      1620
GAK2   ------------------------------------------------------------
GAK1   TCCTTCCTGTGCTTCTGCCGTCTCTTCAGCACCGCGGAGGCCGCCGTGTACATGTTCAGC
GAK    TCCTTCCTGTGCTTCTGCCGTCTCTTCAGCACCGCGGAGGCCGCCGTGTACATGTTCAGC

       1621                                                      1680
GAK2   ------------------------------------------------------------
GAK1   ATGAAGCGCTGCCCACCAGGCATCTGGCCATCCCACAAAAGGTACATCGAGTACATGTGT
GAK    ATGAAGCGCTGCCCACCAGGCATCTGGCCATCCCACAAAAGGTACATCGAGTACATGTGT

       1681                                                      1740
GAK2   ------------------------------------------------------------
GAK1   GACATGGTGGCGGAGGAGCCCATCACACCCCACAGCAAGCCCATCCTGGTGAGGGCCGTG
GAK    GACATGGTGGCGGAGGAGCCCATCACACCCCACAGCAAGCCCATCCTGGTGAGGGCCGTG
```

FIG. 3G

```
      1741                                                      1800
GAK2  ------------------------------------------------------------
GAK1  GTCATGACACCCGTGCCGCTGTTCAGCAAGCAGAGGAGCGGCTGCAGGCCCTTCTGCGAG
GAK   GTCATGACACCCGTGCCGCTGTTCAGCAAGCAGAGGAGCGGCTGCAGGCCCTTCTGCGAG

      1801                                                      1860
GAK2  ------------------------------------------------------------
GAK1  GTCTACGTGGGGGACGAGCGTGTGGCCAGCACCTCCCAGGAGTACGACAAGATGCGGGAC
GAK   GTCTACGTGGGGGACGAGCGTGTGGCCAGCACCTCCCAGGAGTACGACAAGATGCGGGAC

      1861                                                      1920
GAK2  ------------------------------------------------------------
GAK1  TTTAAGATTGAAGATGGCAAAGCGGTGATTCCCCTGGGCGTCACGGTGCAAGGAGACGTG
GAK   TTTAAGATTGAAGATGGCAAAGCGGTGATTCCCCTGGGCGTCACGGTGCAAGGAGACGTG

      1921                                                      1980
GAK2  ------------------------------------------------------------
GAK1  CTCATCGTCATCTATCACGCCCGGTCCACTCTGGGCGGCCGGCTGCAGGCCAAGATGGCA
GAK   CTCATCGTCATCTATCACGCCCGGTCCACTCTGGGCGGCCGGCTGCAGGCCAAGATGGCA

      1981                                                      2040
GAK2  ------------------------------------------------------------
GAK1  TCCATGAAGATGTTCCAGATTCAGTTCCACACGGGGTTTGTGCCTCGGAACGCCACCACT
GAK   TCCATGAAGATGTTCCAGATTCAGTTCCACACGGGGTTTGTGCCTCGGAACGCCACCACT
```

FIG. 3H

```
     2041                                                        2100
GAK2 ------------------------------------------------------------
GAK1 GTGAAATTTGCCAAGTATGACCTGGACGCGTGTGACATTCAAGAAAAATACCCGGATTTA
GAK  GTGAAATTTGCCAAGTATGACCTGGACGCGTGTGACATTCAAGAAAAATACCCGGATTTA

     2101                                                        2160
GAK2 ------------------------------------------------------------
GAK1 TTTCAAGTGAACCTGGAAGTGGAGGTGGAGCCCAGGGACAGGCCGAGCCGGGAAGCCCCA
GAK  TTTCAAGTGAACCTGGAAGTGGAGGTGGAGCCCAGGGACAGGCCGAGCCGGGAAGCCCCA

     2161                                                        2220
GAK2 ------------------------------------------------------------
GAK1 CCATGGAGAACTCGAGCATGAGGGGGCTGAACCCCAAAATCCTGTTTTCCAGCCGGGAG
GAK  CCATGGAGAACTCGAGCATGAGGGGGCTGAACCCCAAAATCCTGTTTTCCAGCCGGGAG

     2221                                                        2280
GAK2 ------------------------------------------------------------
GAK1 GAGCAGCAAGACATTCTGTCTAAGTTTGGGAAGCCGGAGCTTCCCCGGCAGCCTGGCTCC
GAK  GAGCAGCAAGACATTCTGTCTAAGTTTGGGAAGCCGGAGCTTCCCCGGCAGCCTGGCTCC

     2281                                                        2340
GAK2 ------------------------------------------------------------
GAK1 ACGGCTCAGTATGATGCTGGGGCAGGGTCCCCGGAAGCCGAACCCACAGACTCTGACTCA
GAK  ACGGCTCAGTATGATGCTGGGGCAGGGTCCCCGGAAGCCGAACCCACAGACTCTGACTCA
```

FIG. 3I

```
     2341                                                      2400
GAK2 ------------------------------------------------------------
GAK1 CCGCCAAGCAGCAGCGCGGACGCCAGTCGCTTCCTGCACACGCTGGACTGGCAGGAAGAG
GAK  CCGCCAAGCAGCAGCGCGGACGCCAGTCGCTTCCTGCACACGCTGGACTGGCAGGAAGAG

     2401                                                      2460
GAK2 ------------------------------------------------------------
GAK1 AAGGAGGCAGAGACTGGTGCAGAAAATGCCTCTTCCAAGGAGAGCGAGTCTGCCCTGATG
GAK  AAGGAGGCAGAGACTGGTGCAGAAAATGCCTCTTCCAAGGAGAGCGAGTCTGCCCTGATG

     2461                                                      2520
GAK2 ------------------------------------------------------------
GAK1 CAGGACAGAGACGAGAGTGAGGTGTCAGATGAAGGGGGATCCCCGATCTCCAGCGAGGGC
GAK  GAGGACAGAGACGAGAGTGAGGTGTCAGATGAAGGGGGATCCCCGATCTCCAGCGAGGGC

     2521                                                      2580
GAK2 ------------------------------------------------------------
GAK1 CAGGAACCCAGGGCCGACCCAGAGCCCCCCGGCCTGGCAGCAGGGCTGGTGCAGCAGGAC
GAK  CAGGAACCCAGGGCCGACCCAGAGCCCCCCGGCCTGGCAGCAGGGCTGGTGCAGCAGGAC

     2581                                                      2640
GAK2 ------------------------------------------------------------
GAK1 TTGGTTTTTGAGGTGGAGACACCGGCTGTGCTGCCAGAGCCTGTGCCACAGGAAGACGGG
GAK  TTGGTTTTTGAGGTGGAGACACCGGCTGTGCTGCCAGAGCCTGTGCCACAGGAAGACGGG
```

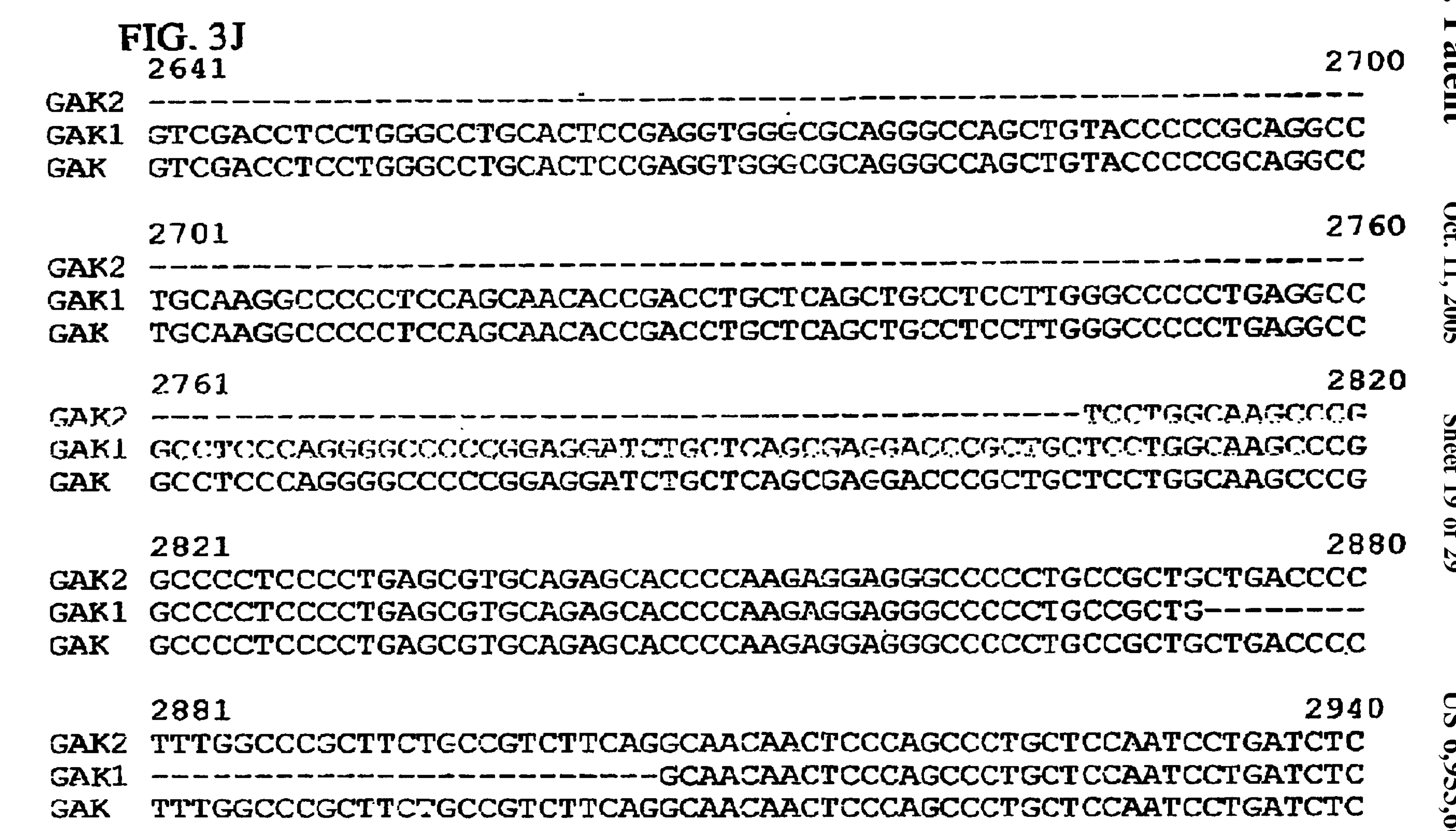
FIG. 3J
2641 2700
GAK2 ------------------------------------------------------------
GAK1 GTCGACCTCCTGGCCTGCACTCCGAGGTGGCGCAGGGCCAGCTGTACCCCCGCAGGCC
GAK GTCGACCTCCTGGCCTGCACTCCGAGGTGGCGCAGGGCCAGCTGTACCCCCGCAGGCC
2701 2760
GAK2 ------------------------------------------------------------
GAK1 TGCAAGGCCCCCTCCAGCAACACCGACCTGCTCAGCTGCCTCCTTGGCCCCCTGAGGCC
GAK TGCAAGGCCCCCTCCAGCAACACCGACCTGCTCAGCTGCCTCCTTGGCCCCCTGAGGCC
2761 2820
GAK2 ----------------------------------------------TCCTGGCAAGCCCG
GAK1 GCCTCCCAGGGGCCCCCGGAGGATCTGCTCAGCGAGGACCCGCTGCTCCTGGCAAGCCCG
GAK GCCTCCCAGGGGCCCCCGGAGGATCTGCTCAGCGAGGACCCGCTGCTCCTGGCAAGCCCG
2821 2880
GAK2 GCCCCTCCCCTGAGCGTGCAGAGCACCCCAAGAGGAGGGCCCCCTGCCGCTGCTGACCCC
GAK1 GCCCCTCCCCTGAGCGTGCAGAGCACCCCAAGAGGAGGGCCCCCTGCCGCTG--------
GAK GCCCCTCCCCTGAGCGTGCAGAGCACCCCAAGAGGAGGGCCCCCTGCCGCTGCTGACCCC
2881 2940
GAK2 TTTGGCCCGCTTCTGCCGTCTTCAGGCAACAACTCCCAGCCCTGCTCCAATCCTGATCTC
GAK1 -------------------------GCAACAACTCCCAGCCCTGCTCCAATCCTGATCTC
GAK TTTGGCCCGCTTCTGCCGTCTTCAGGCAACAACTCCCAGCCCTGCTCCAATCCTGATCTC

FIG. 3K

```
      2941                                                      3000
GAK2  TTCGGCGAATTTCTCAATTCGGACTCTGTGACCGTCCCACCATCCTTCCCGTCTGCCCAC
GAK1  TTCGGCGAATTTCTCAATTCGGACTCTGTGACCGTCCCACCATCCTTCCCGTCTGCCCAC
GAK   TTCGGCGAATTTCTCAATTCGGACTCTGTGACCGTCCCACCATCCTTCCCGTCTGCCCAC

      3001                                                      3060
GAK2  AGCGCTCCGCCCCCATCCTGCAGCGCCGACTTCCTGCACCTGGGGGATCTGCCAGGAGAG
GAK1  AGCGCTCCGCCCCCATCCTGCAGCGCCGACTTCCTGCACCTGGGGGATCTGCCAGGAGAG
GAK   AGCGCTCCGCCCCCATCCTGCAGCGCCGACTTCCTGCACCTGGGGGATCTGCCAGGAGAG

      3061                                                      3120
GAK2  CCCAGCAAGATGACAGCCTCGTCCAGCAACCCAGACCTGCTGGAGGATGGCTGCCTGG
GAK1  CCCAGCAAGATGACAGCCTCGTCCAGCAACCCAGACCTGCTGGAGGATGGCTGCCTGG
GAK   CCCAGCAAGATGACAGCCTCGTCCAGCAACCCAGACCTGCTGGAGGATGGCTGCCTGG

      3121                                                      3180
GAK2  ACCGAGACTGCAGCGTCGGCAGTGGCCCCCACGCCAGCCACAGAAGGCCCCCTCTTCTCT
GAK1  ACCGAGACTGCAGCGTCGGCAGTGGCCCCCACGCCAGCCACAGAAGGCCCCCTCTTCTCT
GAK   ACCGAGACTGCAGCGTCGGCAGTGGCCCCCACGCCAGCCACAGAAGGCCCCCTCTTCTCT

      3181                                                      3240
GAK2  CCTGGAGGTCAGCCGGCCCCTTGTGGCTCTCAGGCCAGCTGGACCAAGTCTCAGAACCCG
GAK1  CCTGGAGGTCAGCCGGCCCCTTGTGGCTCTCAGGCCAGCTGGACCAAGTCTCAGAACCCG
GAK   CCTGGAGGTCAGCCGGCCCCTTGTGGCTCTCAGGCCAGCTGGACCAAGTCTCAGAACCCG
```

FIG. 3L

```
      3241                                                        3300
GAK2  GACCCATTTGCTGACCTTGGCGACCTCAGCTCCGGCCTCCAAGGCTCACCAGCTGGATTT
GAK1  GACCCATTTGCTGACCTTGGCGACCTCAGCTCCGGCCTCCAAGGCTCACCAGCTGGATTT
GAK   GACCCATTTGCTGACCTTGGCGACCTCAGCTCCGGCCTCCAAGGCTCACCAGCTGGATTT

      3301                                                        3360
GAK2  CCTCCTGGGGGCTTCATTCCCAAAACGGCCACCACGGCCAAAGGCAGCAGCTCCTGGCAG
GAK1  CCTCCTGGGGGCTTCATTCCCAAAACGGCCACCACGGCCAAAGGCAGCAGCTCCTGGCAG
GAK   CCTCCTGGGGGCTTCATTCCCAAAACGGCCACCACGGCCAAAGGCAGCAGCTCCTGGCAG

      3361                                                        3420
GAK2  ACAAGTCGGCCGCCAGCCCAGGCGCCTCATGCCCCCTCAGGCCAAGCCGCCCCCAAA
GAK1  ACAAGTCGGCCGCCAGCCCAGGCGCCTCATGGCCCCCTCAGGCCAAGCCGCCCCCAAA
GAK   ACAAGTCGGCCGCCAGCCCAGGCGCCTCATGGCCCCCTCAGGCCAAGCCGCCCCCAAA

      3421                                                        3480
GAK2  GCCTGCACACAGCCAAGGCCTAACTATGCCTCGAACTTCAGTGTGATCGGGGCGCGGGAG
GAK1  GCCTGCACACAGCCAAGGCCTAACTATGCCTCGAACTTCAGTGTGATCGGGGCGCGGGAG
GAK   GCCTGCACACAGCCAAGGCCTAACTATGCCTCGAACTTCAGTGTGATCGGGGCGCGGGAG

      3481                                                        3540
GAK2  GAGCGGGGGGTCCGCGCACCCAGCTTTGCTCAAAAGCCAAAAGTCTCTGAGAACGACTTT
GAK1  GAGCGGGGGGTCCGCGCACCCAGCTTTGCTCAAAAGCCAAAAGTCTCTGAGAACGACTTT
GAK   GAGCGGGGGGTCCGCGCACCCAGCTTTGCTCAAAAGCCAAAAGTCTCTGAGAACGACTTT
```

FIG. 3M

```
      3541                                                        3600
GAK2  GAAGATCTGTTGTCCAATCAAGGCTTCTCCTCCAGGTCTGACAAGAAAGGGCCAAAGACC
GAK1  GAAGATCTGTTGTCCAATCAAGGCTTCTCCTCCAGGTCTGACAAGAAAGGGCCAAAGACC
GAK   GAAGATCTGTTGTCCAATCAAGGCTTCTCCTCCAGGTCTGACAAGAAAGGGCCAAAGACC

      3601                                                        3660
GAK2  ATTGCAGAGATGAGGAAGCAGGACCTGGCTAAAGACACGGACCCACTCAAGCTGAAGCTC
GAK1  ATTGCAGAGATGAGGAAGCAGGACCTGGCTAAAGACACGGACCCACTCAAGCTGAAGCTC
GAK   ATTGCAGAGATGAGGAAGCAGGACCTGGCTAAAGACACGGACCCACTCAAGCTGAAGCTC

      3661                                                        3720
GAK2  CTGGACTGGATTGAGGGCAAGGAGCGGAACATCCGGGCCCTGCTGTCCACGCTGCACACA
GAK1  CTCGACTCGATTCAGGCCAAGGAGCGGAACATCCGGGCCCTGCTGTCCACGCTGCACACA
GAK   CTGGACTGGATTGAGGGCAAGGAGCGGAACATCCGGGCCCTGCTGTCCACGCTGCACACA

      3721                                                        3780
GAK2  GTGCTGTGGGACGGGGAGAGCCGCTGGACGCCCGTGGGCATGGCCGACCTGGTGGCTCCG
GAK1  GTGCTGTGGGACGGGGAGAGCCGCTGGACGCCCGTGGGCATGGCCGACCTGGTGGCTCCG
GAK   GTGCTGTGGGACGGGGAGAGCCGCTGGACGCCCGTGGGCATGGCCGACCTGGTGGCTCCG

      3781                                                        3840
GAK2  GAGCAAGTGAAGAAGCACTATCGCCGCGCGGTGCTGGCCGTGCACCCCGACAAGGCTGCG
GAK1  GAGCAAGTGAAGAAGCACTATCGCCGCGCGGTGCTGGCCGTGCACCCCGACAAGGCTGCG
GAK   GAGCAAGTGAAGAAGCACTATCGCCGCGCGGTGCTGGCCGTGCACCCCGACAAGGCTGCG
```

FIG. 3N

```
     3841                                                        3900
GAK2 GGGCAGCCGTACGAGCAGCACGCCAAGATGATCTTCATGGAGCTGAATGACGCCTGGTCG
GAK1 GGGCAGCCGTACGAGCAGCACGCCAAGATGATCTTCATGGAGCTGAATGACGCCTGGTCG
GAK  GGGCAGCCGTACGAGCAGCACGCCAAGATGATCTTCATGGAGCTGAATGACGCCTGGTCG

     3901                                                        3960
GAK2 GAGTTTGAGAACCAGGGCTCCCGGCCCCTCTTCTGAGGCCGCAGTGGTGGTGGCTGCGCA
GAK1 GAGTTTGAGAACCAGGGCTCCCGGCCCCTCTTCTGAGGCCGCAGTGGTGGTGGCTGCGCA
GAK  GAGTTTGAGAACCAGGGCTCCCGGCCCCTCTTCTGAGGCCGCAGTGGTGGTGGCTGCGCA

     3961                                                        4020
GAK2 CACAGCTCCACAGGTTGGGAGCCGTCGTGGGACCTGGGTCCCCACCGTGAGGACCCCGTG
GAK1 CACAGCTCCACAGGTTGGGAGCCGTCGTGGGACCTGGGTCCCCACCGTGAGGACCCCGTG
GAK  CACAGCTCCACAGGTTGGGAGCCGTCGTGGGACCTGGGTCCCCACCGTGAGGACCCCGTG

     4021                                                        4080
GAK2 GGCGACAGCAGGTGTGGCCAGGGTGGGGCTCCGAGCCCCGGGTCACCGCCCGCCCAGCGT
GAK1 GGCGACAGCAGGTGTGGCCAGGGTGGGGCTCCGAGCCCCGGGTCACCGCCCGCCCAGCGT
GAK  GGCGACAGCAGGTGTGGCCAGGGTGGGGCTCCGAGCCCCGGGTCACCGCCCGCCCAGCGT

     4081                                                        4140
GAK2 TCCAGGCACATGAAGAGAAAGCATTCCAAAGCCTCTGATTGTTGTTTCCTTTTTCTCCTC
GAK1 TCCAGGCACATGAAGAGAAAGCATTCCAAAGCCTCTGATTGTTGTTTCCTTTTTCTCCTC
GAK  TCCAGGCACATGAAGAGAAAGCATTCCAAAGCCTCTGATTGTTGTTTCCTTTTTCTCCTC
```

FIG. 3O

```
      4141                                                        4200
GAK2  CCGAAGGAACAGCTGATTCATGCTCCTCCCGCAATTGTCACGTCTGTGATTTATTTGGTG
GAK1  CCGAAGGAACAGCTGATTCATGCTCCTCCCGCAATTGTCACGTCTGTGATTTATTTGGTG
GAK   CCGAAGGAACAGCTGATTCATGCTCCTCCCGCAATTGTCACGTCTGTGATTTATTTGGTG

      4201                                                        4260
GAK2  TTTCGGGCGTGGCCTCTGGAGCCCCGGCACGTGGTGGGCCACGCTGCTGGCGCTCATGGG
GAK1  TTTCGGGCGTGGCCTCTGGAGCCCCGGCACGTGGTGGGCCACGCTGCTGGCGCTCATGGG
GAK   TTTCGGGCGTGGCCTCTGGAGCCCCGGCACGTGGTGGGCCACGCTGCTGGCGCTCATGGG

      4261                                                        4320
GAK2  CCCTGGTGTTTGCACCGCACTTTGTAATCAGTCCCGTGGTTGTCTGTACAGAATTAAACT
GAK1  CCCTGGTGTTTGCACCGCACTTTGTAATCAGTCCCGTGGTTGTCTGTACAGAATTAAACT
GAK   CCCTGGTGTTTGCACCGCACTTTGTAATCAGTCCCGTGGTTGTCTGTACAGAATTAAACT

      4321
GAK2  ATTTTCCGATG    1646
GAK1  ATTTTCCGATG    4298
GAK   ATTTTCCGATG    4331
```

FIG. 4A

```
     1                                                          60
GAK2 MSLLQSALDFLAGPGSLGGASGRDQSDFVGQTVELGELRL--------------------
GAK1 MSLLQSALDFLAGPGSLGGASGRDQSDFVGQTVELGELRLRVRRVLAEGGFAFVYEAQDV
GAK  MSLLQSALDFLAGPGSLGGASGRDQSDFVGQTVELGELRLRVRRVLAEGGFAFVYEAQDV

     61                                                        120
GAK2 ------------------------------------------------------------
GAK1 GSGREYALKRLLSNEEEKNRAIIQEVCFMKKLSGHPNIVQFCSAASIGKEESDTGQAEFL
GAK  GSGREYALKRLLSNEEEKNRAIIQEVCFMKKLSGHPNIVQFCSAASIGKEESDTGQAEFL

     121                                                       180
GAK2 ------------------------------------------------------------
GAK1 LLTELCKGQLVEFLKKMESRGPLSCDTVLKIFYQTCRAVQHMHRQKPPIIHRDLKVENLL
GAK  LLTELCKGQLVEFLKKMESRGPLSCDTVLKIFYQTCRAVQHMHRQKPPIIHRDLKVENLL

     181                                                       240
GAK2 ------------------------------------------------------------
GAK1 LSNQGTIKLCDFGSATTISHYPDYSWSAQRRALVEEEITRNTTPMYRTPEIIDLYSNFPI
GAK  LSNQGTIKLCDFGSATTISHYPDYSWSAQRRALVEEEITRNTTPMYRTPEIIDLYSNFPI
```

FIG. 4B

```
      241                                                         300
GAK2  ------------------------------------------------------------
GAK1  GEKQDIWALGCILYLLCFRQHPFEDGAKLRIVNGKYSIPPHDTQYTVFHSLIRAMLQVNP
GAK   GEKQDIWALGCILYLLCFRQHPFEDGAKLRIVNGKYSIPPHDTQYTVFHSLIRAMLQVNP

      301                                                         360
GAK2  ------------------------------------------------------------
GAK1  EERLSIAEVVHQLQEIAAARNVNPKSPITELLEQNGGYGSATLSRGPPPPVGPAGSGYSG
GAK   EERLSIAEVVHQLQEIAAARNVNPKSPITELLEQNGGYGSATLSRGPPPPVGPAGSGYSG

      361                                                         420
GAK2  ............................................................
GAK1  GLALAEYDQPYGGFLDILRGGTERLFTNLKDTSSKVIQSVANYAKGDLDISYITSRIAVM
GAK   GLALAEYDQPYGGFLDILRGGTERLFTNLKDTSSKVIQSVANYAKGDLDISYITSRIAVM

      421                                                         480
GAK2  ------------------------------------------------------------
GAK1  SFPAEGVESALKNNIEDVRLFLDSKHPGHYAVYNLSPRTYRPSRFHNRVSECGWAARRAP
GAK   SFPAEGVESALKNNIEDVRLFLDSKHPGHYAVYNLSPRTYRPSRFHNRVSECGWAARRAP

      481                                                         540
GAK2  ------------------------------------------------------------
GAK1  HLHTLYNICRNMHAWLRQDHKNVCVVHCMDGRAASAVAVCSFLCFCRLFSTAEAAVYMFS
GAK   HLHTLYNICRNMHAWLRQDHKNVCVVHCMDGRAASAVAVCSFLCFCRLFSTAEAAVYMFS
```

FIG. 4C

```
     541                                                        600
GAK2 ------------------------------------------------------------
GAK1 MKRCPPGIWPSHKRYIEYMCDMVAEEPITPHSKPILVRAVVMTPVPLFSKQRSGCRPFCE
GAK  MKRCPPGIWPSHKRYIEYMCDMVAEEPITPHSKPILVRAVVMTPVPLFSKQRSGCRPFCE

     601                                                        660
GAK2 ------------------------------------------------------------
GAK1 VYVGDERVASTSQEYDKMRDFKIEDGKAVIPLGVTVQGDVLIVIYHARSTLGGRLQAKMA
GAK  VYVGDERVASTSQEYDKMRDFKIEDGKAVIPLGVTVQGDVLIVIYHARSTLGGRLQAKMA

     661                                                        720
GAK2 ------------------------------------------------------------
GAK1 SMKMFQIQFHTGFVPRNATTVKFAKYDLDACDIQEKYPDLFQVNLEVEVEPRDRPSREAP
GAK  SMKMFQIQFHTGFVPRNATTVKFAKYDLDACDIQEKYPDLFQVNLEVEVEPRDRPSREAP

     721                                                        780
GAK2 ------------------------------------------------------------
GAK1 PWENSSMRGLNPKILFSSREEQQDILSKFGKPELPRQPGSTAQYDAGAGSPEAEPTDSDS
GAK  PWENSSMRGLNPKILFSSREEQQDILSKFGKPELPRQPGSTAQYDAGAGSPEAEPTDSDS

     781                                                        840
GAK2 ------------------------------------------------------------
GAK1 PPSSSADASRFLHTLDWQEEKEAETGAENASSKESESALMEDRDESEVSDEGGSPISSEG
GAK  PPSSSADASRFLHTLDWQEEKEAETGAENASSKESESALMEDRDESEVSDEGGSPISSEG
```

FIG. 4D

```
     841                                                         900
GAK2 ------------------------------------------------------------
GAK1 QEPRADPEPPGLAAGLVQQDLVFEVETPAVLPEPVPQEDGVDLLGLHSEVGAGPAVPPQA
GAK  QEPRADPEPPGLAAGLVQQDLVFEVETPAVLPEPVPQEDGVDLLGLHSEVGAGPAVPPQA

     901                                                         960
GAK2 -----------------------------------LLASPAPPLSVQSTPRGGPPAAADP
GAK1 CKAPSSNTDLLSCLLGPPEAASQGPPEDLLSEDPLLLASPAPPLSVQSTPRGGPPAA---
GAK  CKAPSSNTDLLSCLLGPPEAASQGPPEDLLSEDPLLLASPAPPLSVQSTPRGGPPAAADP

     961                                                        1020
GAK2 FGPLLPSSCNNSQPCSNPDLFGEFLNSDSVTVPPSFPSAHSAPPPSCSADFLHLGDLPGE
GAK1 --------GNNSQPCSNPDLFGEFLNSDSVTVPPSFPSAHSAPPPSCSADFLHLGDLPGE
GAK  FGPLLPSSGNNSQPCSNPDLFGEFLNSDSVTVPPSFPSAHSAPPPSCSADFLHLGDLPGE

     1021                                                       1080
GAK2 PSKMTASSSNPDLLGGWAAWTETAASAVAPTPATEGPLFSPGGQPAPCGSQASWTKSQNP
GAK1 PSKMTASSSNPDLLGGWAAWTETAASAVAPTPATEGPLFSPGGQPAPCGSQASWTKSQNP
GAK  PSKMTASSSNPDLLGGWAAWTETAASAVAPTPATEGPLFSPGGQPAPCGSQASWTKSQNP

     1081                                                       1140
GAK2 DPFADLGDLSSGLQGSPAGFPPGGFIPKTATTAKGSSSWQTSRPPAQGASWPPQAKPPPK
GAK1 DPFADLGDLSSGLQGSPAGFPPGGFIPKTATTAKGSSSWQTSRPPAQGASWPPQAKPPPK
GAK  DPFADLGDLSSGLQGSPAGFPPGGFIPKTATTAKGSSSWQTSRPPAQGASWPPQAKPPPK
```

FIG. 4E

```
      1141                                                        1200
GAK2  ACTQPRPNYASNFSVIGAREERGVRAPSFAQKPKVSENDFEDLLSNQGFSSRSDKKGPKT
GAK1  ACTQPRPNYASNFSVIGAREERGVRAPSFAQKPKVSENDFEDLLSNQGFSSRSDKKGPKT
GAK   ACTQPRPNYASNFSVIGAREERGVRAPSFAQKPKVSENDFEDLLSNQGFSSRSDKKGPKT

      1201                                                        1260
GAK2  IAEMRKQDLAKDTDPLKLKLLDWIEGKERNIRALLSTLHTVLWDGESRWTPVGMADLVAP
GAK1  IAEMRKQDLAKDTDPLKLKLLDWIEGKERNIRALLSTLHTVLWDGESRWTPVGMADLVAP
GAK   IAEMRKQDLAKDTDPLKLKLLDWIEGKERNIRALLSTLHTVLWDGESRWTPVGMADLVAP

      1261
GAK2  EQVKKHYRRAVLAVHPDKAAGQPYEQHAKMIFMELNDAWSEFENQGSRPLF     416
GAK1  EQVKKHYRRAVLAVHPDKAAGQPYEQHAKMIFMELNDAWSEFENQGSRPLF    1300
GAK   EQVKKHYRRAVLAVHPDKAAGQPYEQHAKMIFMELNDAWSEFENQGSRPLF    1311
```

HUMAN GAK-RELATED GENE VARIANTS ASSOCIATED WITH LUNG CANCER

FIELD OF THE INVENTION

The invention relates to the nucleic acid of novel human GAK-related gene variants and the polypeptide encoded thereby, the preparation process thereof, and the uses of the same in diagnosing diseases associated with the variants, in particular, homeostasis impairment-related diseases and non-small cell lung cancer, e.g. large cell lung cancer.

BACKGROUND OF THE INVENTION

Lung cancer is one of the major causes of cancer-related deaths in the world. There are two primary types of lung cancers: small cell lung cancer (SCLC) and non-small cell lung cancer (NSCLC) (Carney, (1992a) Curr. Opin. Oncol. 4: 292–8). Small cell lung cancer accounts for approximately 25% of lung cancer and spreads aggressively (Smyth et al. (1986) Q J Med. 61: 969–76; Carney, (1992b) Lancet 339: 843–6). Non-small cell lung cancer represents the majority (about 75%) of lung cancer and is further divided into three main subtypes: squamous cell carcinoma, adenocarcinoma, and large cell carcinoma (Ihde and Minna, (1991) Cancer 15: 105–54). In recent years, much progress has been made toward understanding the molecular and cellular biology of lung cancers. Many important contributions have been made by the identification of several key genetic factors associated with lung cancers. However, the treatments of lung cancers still mainly depend on surgery, chemotherapy, and radiotherapy. This is because the molecular mechanisms underlying the pathogenesis of lung cancers remain largely unclear.

A recent hypothesis suggested that lung cancer is caused by genetic mutations of at least 10 to 20 genes (Sethi, (1997) BMJ. 314: 652–655). Therefore, future strategies for the prevention and treatment of lung cancers will be focused on the elucidation of these genetic substrates, in particular, the genes associated with the cell cycle regulation in lung cancers since it is believed that dysregulation of cell cycle may lead to the initiation and progression of cancers. Cyclins, regulators of cell cycle in eukaryotic cells (Hunter and Pines, (1991) Cell 66:1071–4), have been shown to be associated with cancers (Hunter and Pines, (1991) Cell 66:1071–4; Lammie et al. (1991) Oncogene 6:439–44; Jiang et al. (1992) Cancer Res 52:2980–3; Keyomarsi and Pardee, (1993) Proc Natl Acad Sci U S A 90:1112–6; Weinstat-Saslow et al. (1995) Nat Med 1:1257–60). Cyclin G, a member of the cyclin family, has been shown to be associated with the carcinogenic process (Skotzko et al. (1995) Cancer Res 55:5493–8; Reimer et al. (1999) J Biol Chem 274:11022–9) mediated via p53 (a tumor suppressor gene) cell growth regulatory pathways (Okamoto and Beach, (1994) EMBO J 13:4816–22; Home et al. (1996) J Biol Chem 271:6050–61; Bates et al. (1996) Oncogene 13:1103–9; Smith et al. (1997) Exp Cell Res 230:61–8). The involvement of p53 gene in NSCLC (Kohno et al. (1999) Cancer 85: 341–7) suggests that the genes associated with cyclin G may be involved in the carcinogenesis of lung cancers. Therefore, the cyclin G-associated protein kinase (GAK), a partner of cyclin G (Kanaoka et al. (1997) FEBS Lett 402:73–80), is expected to be an important molecule for lung cancers.

The human GAK gene (Kimura et al. (1997) Genomics 44:179–87) contains an open reading frame (ORP) of 3933 bp encoding 1311 amino acids. Sequence analysis demonstrated that GAK contains a Ser/Thr kinase domain, a tensin/auxilin homologous domain, and a Tyr phosphorylation target site. Using FISH technique, GAK was assigned to the chromosome 4p16 (Kimura et al. (1997) Genomics 44:179–87), a chromosomal region frequently altered in lung cancers (Michelland et al. (1999) Cancer Genet Cytogenet 114:22–30). Taken together with the discovery of gene variants of NOC2 (localized on chromosome 17p) as potential diagnostic markers for lung cancers (U.S. patent Ser. No. 09/964,275), we believe that the discovery of GAK-related gene variants may also be important targets for diagnostic markers of lung cancers.

SUMMARY OF THE INVENTION

The present invention provides two GAK gene variants (GAK1 and GAK2) present in human lung tissues. The nucleotide sequences of these variants and the polypeptide sequences encoded thereby can be used for the diagnosis of diseases associated with the deficiency of GAK gene, in particular, homeostasis impairment-related diseases and non-small cell lung cancer, e.g. large cell lung cancer.

The invention further provides an expression vector and host cell for expressing the polypeptides of the invention.

The invention further provides a method for producing the polypeptides encoded by the variants of the invention.

The invention further provides an antibody specifically binding to the polypeptides.

The invention also provides methods for diagnosing diseases associated with GAK gene, in particular, homeostasis impairment-related diseases and non-small cell lung cancer, e.g. large cell lung cancer.

BRIEF DESCRIPTION OF THE DRAWINGS

FIGS. 1A–F show the nucleic acid sequence (SEQ ID NO:1) and amino acid sequence (SEQ ID NO:2) of GAK1.

FIGS. 2A–C show the nucleic acid sequence (SEQ ID NO:3) and amino acid sequence (SEQ ID NO:4) of GAK2.

FIGS. 3A–O show the nucleotide sequence alignment between the human GAK gene and its related gene variants (GAK1 and GAK2).

FIGS. 4A–E show the amino acid sequence alignment between the human GAK protein and its related gene variants (GAK1 and GAK2).

DETAILED DESCRIPTION OF THE INVENTION

According to the present invention, all technical and scientific terms used have the same meanings as commonly understood by persons skilled in the art.

The term "antibody" used herein denotes intact molecules (a polypeptide or group of polypeptides) as well as fragments thereof, such as Fab, $R(ab')_2$, and Fv fragments, which are capable of binding the epitopic determinant. Antibodies are produced by specialized B cells after stimulation by an antigen. Structurally, an antibody consists of four subunits including two heavy chains and two light chains. The internal surface shape and charge distribution of the antibody binding domain is complementary to the features of an antigen. Thus, the antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389–3402)" used herein denotes programs for evaluation of homologies between a query sequence (amino or nucleic acid) and a test sequence as described by Altschul et al. (Nucleic Acids Res. 25: 3389–3402, 1997). Specific BLAST programs are described as follows:

(1) BLASTN compares a nucleotide query sequence with a nucleotide sequence database;

(2) BLASTP compares an amino acid query sequence with a protein sequence database;

(3) BLASTX compares the six-frame conceptual translation products of a query nucleotide sequence with a protein sequence database;

(4) TBLASTN compares a query protein sequence with a nucleotide sequence database translated in all six reading frames; and (5) TBLASTX compares the six-frame translations of a nucleotide query sequence with the six-frame translations of a nucleotide sequence database.

The term "cDNA" used herein denotes nucleic acids synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATGGACTTACT-3' binds to the complementary sequence 5'-AGTAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequences derived from either 5' or 3' end of a cDNA.

The term "expression vector" used herein denotes nucleic acid constructs which contain a cloning site for introducing the DNA into the vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR) used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "protein" or "polypeptide" used herein denotes a sequence of amino acids in a specific order that can be encoded by a gene or by a recombinant DNA. It can also be chemically synthesized.

The term "nucleic acid sequence" or "polynucleotide" used herein denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein denotes a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

According to the present invention, the polypeptides of two novel human GAK-related gene variants and fragments thereof, and the nucleic acid sequences encoding the same are provided.

According to the present invention, the human GAK cDNA sequence was used to query the human lung EST databases (a normal lung and a large cell lung cancer) using BLAST program to search for GAK-related gene variants. Two human cDNA partial sequences (i.e., ESTs) deposited in the databases showing similarity to GAK were isolated and sequenced.

These clones (named GAK1 and GAK2) were both isolated from large cell lung cancer cDNA library. FIGS. 1A–F and 2A–C show the nucleic acid sequences (SEQ ID NOs:1, and 3) of the variants and corresponding amino acid sequences (SEQ ID NOs:2, and 4) encoded thereby.

The full-length of the GAK1 cDNA is a 4308 bp clone containing a 3900 bp open reading frame (ORF) extending from nucleotides 11 to 3910, which corresponds to an encoded protein of 1300 amino acid residues with a predicted molecular mass of 142.1 kDa. The full-length of the GAK2 cDNA is a 1740 bp clone containing a 1248 bp ORF extending from nucleotides 95 to 1342, which corresponds to an encoded protein of 416 amino acid residues with a predicted molecular mass of 43.9 kDa. The sequences around the initiation ATG codon of GAK1 (located at nucleotides 11 to 13) and of GAK2 (located at nucleotides 95 to 97) were matched with the Kozak consensus sequence (A/GCCATGG) (Kozak, (1987) Nucleic Acids Res. 15: 8125–48; Kozak, (1991) J Cell Biol. 115: 887–903.). To determine the variations (insertion/deletion) in sequences of GAK1 and GAK2 cDNA clones, an alignment of GAK nucleotide/amino acid sequence with these clones was performed (FIGS. 3A–O and 4A–E). Two major genetic deletions were found in the aligned sequences. GAK1 is an in-frame 33 bp (encoding 11 amino acid residues) deletion in the coding regions of GAK sequence from nucleotides 2873 to 2905. GAK2 is an in-frame 2685 bp (encoding 895 amino acid residues) deletion in the coding regions of GAK sequence from nucleotides 122 to 2806.

In the present invention, a search of ESTs deposited in dbEST (Boguski et al., (1993) Nat Genet. 4: 332–3) at NCBI was performed. ESTs matched to the sequence fragments that contain genetic changes (deletion) were identified. Five ESTs were found to confirm the missing region described in GAK1 and GAK2. Four ESTs (GenBank accession number BG746688; BG333001; BG821224; B1026835), confirmed the absence of 33 bp region on GAK1 nucleotide sequence, was found to be isolated from cDNA libraries derived from large cell lung cancer, colon adenocarcinoma, and marrow tissues. This suggests that the absence of 33 bp fragment may serve as an important indicator for cancers. The other one EST (GenBank accession number BE619037), confirmed the absence of 2685 bp region on GAK2 nucleotide sequence, was found to be isolated from a large cell lung cancer cDNA library. This suggests that the absence of the 2685 bp fragment may be a useful marker for large cell lung cancer diagnosis.

Therefore, any nucleotide fragments comprising nucleotides 2870 to 2875 (encoding amino acid residues 954 to 955) of GAK1 and nucleotides 119 to 124 (encoding amino acid residue 9 to 10) of GAK2 may be used as probes for determining the presence of the variants under high stringency conditions. An alternative approach is that any set of primers for amplifying the fragment containing nucleotides 2870 to 2875 of GAK1 and nucleotides 119 to 124 of GAK2 may be used for determining the presence of the variants.

A search of the predicted protein products of GAK1 against the profile entries in PROSITE (ScanProsite) shows that GAK1 contains five N-glycosylation sites (amino acid residues 677 to 680, 724 to 727, 809 to 812, 959 to 962, and 1141 to 1144), one cAMP- and cGMP-dependent protein kinase phosphorylation site (amino acid residues 90 to 93), seventeen protein kinase C phosphorylation sites (amino acid residues 21 to 23, 62 to 64, 155 to 157, 186 to 188, 382 to 384, 393 to 395, 414 to 416, 456 to 458, 459 to 461, 540 to 542, 551 to 553, 661 to 663, 680 to 682, 726 to 728, 737 to 739, 811 to 813, and 1110 to 1112), seventeen casein kinase II phosphorylation sites (amino acid residues 6 to 9, 21 to 24, 62 to 65, 73 to 76, 305 to 308, 530 to 533, 611 to 614, 737 to 741, 776 to 779, 784 to 787, 805 to 808, 811 to 814, 906 to 909, 965 to 968, 1018 to 1021, 1165 to 1168, and 1180 to 1183), one Tyrosine kinase phosphorylation site (amino acid residues 405 to 412), seventeen N-myristoylation sites (amino acid residues 15 to 20, 18 to 23, 193 to 198, 336 to 341, 355 to 360, 361 to 366, 426 to 431, 547 to 552, 769 to 774, 806 to 811, 833 to 838, 851 to 856, 891 to 896, 952 to 957, 1024 to 1029, 1058 to 1063, and 1084 to 1089), and one Serine/Threonine protein kinases active-site signature (amino acid residues 169 to 181). Scanning a sequence against protein profile databases (ProfileScan) indicates that GAK1 protein contains a protein kinase domain (amino acid residues 40 to 314) and a proline-rich region (amino acid residues 894 to 1136). A comparison of the protein domain sequence search between GAK1 and GAK shows that GAK1 sequence is only 33 bp (11aa) shorter than GAK sequence. The results indicate that the segment deleted in GAK1 sequence is located on the proline-rich region. The partial deletion of the proline-rich region observed in GAK1 suggests that the functional role of GAK1 may not be the same as GAK. However, it is believable that the presence of GAK1 may be associated with lung cancer.

A search of the predicted protein products of GAK2 against the profile entries in PROSITE (ScanProsite) shows that GAK2 protein contains two N-glycosylation sites (amino acid residues 75 to 78 and 257 to 260), six protein kinase C phosphorylation sites (amino acid residues 21 to 23, 54 to 56, 217 to 219, 226 to 228, 295 to 297, and 298 to 300), six casein kinase II phosphorylation sites (amino acid residues 6 to 9, 21 to 24, 81 to 84, 134 to 137, 281 to 284, and 296 to 299), six N-myristoylation sites (amino acid residues 15 to 20, 18 to 23, 57 to 62, 140 to 145, 174 to 179, and 200 to 205), and one TonB-dependent receptor proteins signature (amino acid residues 1 to 100). Scanning a sequence against protein profile databases (ProfileScan) indicates that GAK2 protein contains a proline-rich region (amino acid residues 45 to 252). A comparison of GAK2 and GAK in protein domain sequence search indicates that GAK2 contain a TonB-dependent receptor proteins signature being different from GAK, and suggests that this in-frame 895aa sequence deletion has made the functional role of GAK2 different from that of GAK. It should be noted that the sequence of GAK2 was found to match a complete sequence of a cDNA clone deposited in GenBank (accession number BC008668). This clone was isolated from a cDNA library prepared using lung large cell carcinoma tissue.

The presence of TonB-dependent receptor proteins signature in GAK2 suggests that GAK2 may play a role in iron regulation since the biological function of TonB-dependent receptor protein has been identified to relate to the acquisition of iron in the host cells infected by bacteria (Lundrigan and Kadner, (1986) J Biol Chem 261:10797–801; Schramm et al. (1987) J Bacteriol 169:3350–7; Ogunnariwo and Schryvers, (2001) J Bacteriol 183:890–6). Impairment of iron homeostasis has been reported to be associated with the increase of the risk of many diseases such as cancer (Weinberg (1996) Eur J Cancer Prev 5:19–36), acute myocardial infarction (Tuomainen ET AL. (1998) Circulation 97:1461–6); neural disorder (Earley et al. (2000) J Neurosci Res 62:623–8), sudden infant death (Weinberg (2001) Med Hypotheses 56:731–4; and infection (Weinberg (1992) Life Sci 50:1289–97). Therefore, the presence of GAK2 may be a useful diagnostic marker not only for lung cancers (in particular large cell lung cancer) but also for iron homeostasis impairment-related diseases.

According to the present invention, the polypeptides of the human GAK-related gene variants and the fragments thereof may be produced through genetic engineering techniques. In this case, they are produced by appropriate host cells that have been transformed by DNAs that code the polypeptides or the fragments thereof. The nucleotide sequence encoding the polypeptide of the human GAK-related gene variants or the fragments thereof is inserted into an appropriate expression vector, i.e., a vector which contains the necessary elements for the transcription and translation of the inserted coding sequence in a suitable host. The nucleic acid sequence is inserted into the vector in a manner that it will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing the sequences encoding the polypeptides of the human GAK-related gene variants and appropriate transcriptional/translational control elements. These methods may include in vitro recombinant DNA and synthetic techniques, and in vivo genetic recombinants. (See, e.g., Sambrook, J. Cold Spring Harbor Press, Plainview N.Y., ch. 4, 8, and 16–17; Ausubel, R. M. et al. (1995) Current protocols in Molecular Biology, John Wiley & Sons, New York N.Y., ch. 9, 13, and 16.)

A variety of expression vector/host systems may be utilized to express the polypeptide-coding sequence. These include, but are not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is *E. coli.*

Alternatively, the polypeptides of the GAK1 and GAK2, or the fragments thereof may be synthesized by using chemical methods. For example, peptide synthesis can be performed using various solid-phase techniques (Roberge, J. Y. et al. (1995) Science 269: 202 to 204). Automated synthesis may be achieved using the ABI 431A peptide synthesizer (Perkin-Elmer).

According to the present invention, the fragments of the polypeptides and the nucleic acid sequences of the human GAK1 and GAK2 are used as immunogens and primers or probes, respectively. It is preferable to use the purified fragments of the human GAK1 and GAK2. The fragments may be produced by enzyme digestion, chemical cleavage of isolated or purified polypeptide or nucleic acid sequences, or chemical synthesis and then may be isolated or purified. Such isolated or purified fragments of the polypeptides and nucleic acid sequences can be directly used as immunogens and primers or probes, respectively.

The present invention further provides the antibodies which specifically bind one or more out-surface epitopes of the polypeptides of the human GAK1 and GAK2.

According to the present invention, immunization of mammals with immunogens described herein, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. Nos. 4,271,145 and 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using column chromatography methods well known to those skilled in the art.

According to the present invention, antibody fragments which contain specific binding sites for the polypeptides or the fragments thereof may also be generated. For example, such fragments include, but are not limited to, $F(ab')_2$ fragments produced by pepsin digestion of the antibody molecule and Fab fragments generated by reducing the disulfide bridges of the $F(ab')_2$ fragments.

Many gene variants have been found to be associated with diseases (Stallings-Mann et al., (1996) Proc Natl Acad Sci U S A 93: 12394–9; Liu et al., (1997) Nat Genet 16:328–9; Siffert et al., (1998) Nat Genet 18: 45 to 8; Lukas et al., (2001) Cancer Res 61: 3212 to 9). Since GAK is associated with a region (chromosome 4p) of frequent loss of heterozygosity in NSCLC, it is advisable that the gene variants of the present invention, which have genetic deletion of nucleotide/amino acid sequences, may result in cancer development and may be useful as markers for the diagnosis of human lung cancer. Based on the cDNA libraries of the matched ESTs, GAK2 can be specifically associated with large cell lung cancer whereas GAK1 can be associated with general cancers. Thus, the expression level of GAK1 or GAK2 relative to GAK may be a useful indicator for screening of patients suspected of having cancers or large cell lung cancer, respectively. This suggests that the index of relative expression level (mRNA or protein) may associate with an increased susceptibility to cancers or NSCLC, more preferably, large cell lung cancer. The fragments of GAK1 and GAK2 transcripts (mRNAs) may be detected by RT-PCR approach. Polypeptides of GAK1 and GAK2 may be determined by the binding of antibodies to these polypeptides. These approaches may be performed in accordance with conventional methods well known by persons skilled in the art.

The subject invention also provides methods for diagnosing the diseases associated with the deficiency of GAK in a mammal, in particular, homeostasis impairment-related diseases and non-small cell lung cancer, e.g. large cell lung cancer.

The method for diagnosing the diseases associated with the deficiency of GAK may be performed by detecting the nucleotide sequences of GAK1 and GAK2 variants of the invention, which comprises the steps of: (1) extracting total RNA of cells obtained from a mammal; (2) amplifying the RNA by reverse transcriptase-polymerase chain reaction (RT-PCR) with a set of primers to obtain a cDNA comprising the fragments comprising nucleotides 2870 to 2875 of SEQ ID NO: 1 or nucleotides 119 to 124 of SEQ ID NO: 3; and (3) detecting whether the cDNA sample is obtained. If necessary, the amount of the obtained cDNA sample may be detected.

In the above embodiment, one of the primers may be designed to have a sequence comprising the nucleotides 2870 to 2875 of SEQ ID NO: 1 the nucleotides 119 to 124 of SEQ ID NO: 3, and the other may be designed to have a sequence complementary to the nucleotides of SEQ ID NO: 1 at any other locations downstream of nucleotide 2875 or to have a sequence complementary to the nucleotides of SEQ ID NO: 3 at any other locations downstream of nucleotide 124. Alternatively, one of the primers may be designed to have a sequence complementary to the nucleotides of SEQ ID NO: 1 containing nucleotides 2870 to 2875 or to have a sequence complementary to the nucleotides of SEQ ID NO: 3 containing nucleotides 119 to 124, and the other may be designed to have a sequence comprising the nucleotides of SEQ ID NO: 1 at any other locations upstream of nucleotide 2870 or to have a sequence comprising the nucleotides of SEQ ID NO: 3 at any other locations upstream of nucleotide 119. In this case, only GAK1 or GAK2 will be amplified.

Alternatively, one of the primers may be designed to have a sequence comprising the nucleotides of SEQ ID NO: 1 upstream of nucleotide 2872 or to have a sequence comprising the nucleotides of SEQ ID NO: 3 upstream of nucleotide 121, and the other may be designed to have a sequence complementary to the nucleotides of SEQ ID NO: 1 downstream of nucleotide 2873 or to have a sequence complementary to the nucleotides of SEQ ID NO: 3 downstream of nucleotide 122. Alternatively, one of the primers may be designed to have a sequence complementary to the nucleotides of SEQ ID NO: 1 upstream of nucleotide 2872 or to have a sequence complementary to the nucleotides of SEQ ID NO: 3 upstream of nucleotide 121, and the other may be designed to have a sequence comprising the nucleotides of SEQ ID NO: 1 downstream of nucleotide 2873 or to have a sequence comprising the nucleotides of SEQ ID NO: 3 downstream of nucleotide 122. In this case, GAK, GAK1 and GAK2 will be amplified. The length of the PCR fragment from GAK1 will be 33 bp shorter than that from GAK, and that of the PCR fragment from GAK2 will be 2685 bp shorter than that from GAK.

Preferably, the primers of the invention contain 15 to 30 nulceotides.

Total RNA may be isolated from patient samples by using TRIZOL reagents (Life Technology). Tissue samples (e.g., biopsy samples) are powdered under liquid nitrogen before homogenization. RNA purity and integrity are assessed by absorbance at 260/280 nm and by agarose gel electrophoresis. The set of primers designed to amplify the expected size of specific PCR fragments of GAK 1 or GAK2 can be used. PCR fragments are analyzed on a 1% agarose gel using five microliters (10%) of the amplified products. To determine the expression levels for each gene variants, the intensity of the PCR products may be determined by using the Molecular Analyst program (version 1.4.1; Bio-Rad).

The RT-PCR experiment may be performed according to the manufacturer instructions (Boehringer Mannheim). A 50 $\mu$l reaction mixture containing 2 $\mu$l total RNA (0.1 $\mu$g/l), 1 $\mu$l each primer (20 pM), 1 $\mu$l each dNTP (10 mM), 2.5 $\mu$l DTT solution (100 mM), 10 $\mu$l 5×RT-PCR buffer, 1 $\mu$l enzyme mixture, and 28.5 $\mu$l sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

Another embodiment of the method for diagnosing the diseases associated with the deficiency of GAK is performed by detecting the nucleotide sequence of GAK1 or GAK2 variant of the invention which comprises the steps of: (1) extracting total RNA from a sample obtained from the mammal; (2) amplifying the RNA by reverse transcriptase-polymerase chain reaction (RT-PCR) to obtain a cDNA sample; (3) bringing the cDNA sample into contact with the nucleic acid selected from the group consisting of SEQ ID NOs: 1 and 3, and the fragments thereof; and (4) detecting whether the cDNA sample hybridizes with the nucleic acid of SEQ ID NOs: 1 or 3, or the fragments thereof. If necessary, the amount of hybridized sample may be detected.

The expression of gene variants can be analyzed using Northern Blot hybridization approach. Specific fragment comprising nucleotides 957 to 958 of SEQ ID NO: 1 or nucleotides 119 to 124 of SEQ ID NO: 3 may be amplified by polymerase chain reaction (PCR) using primer set designed for RT-PCR. The amplified PCR fragment may be labeled and serve as a probe to hybridize the membranes containing total RNAs extracted from the samples under the conditions of 55° C. in a suitable hybridization solution for 3 hours. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of gene variants (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the method for diagnosing the diseases associated with the gene variants (GAK1 and GAK2) of the invention may also be performed by detecting the polypeptides of the gene variants. For instance, the polypeptides in protein samples obtained from the mammal may be determined by, but is not limited to, the immunoassay wherein the antibody specifically binding to the polypeptides of the invention is contacted with the protein samples, and the antibody-polypeptide complex is detected. If necessary, the amount of the antibody-polypeptide complexes can be determined.

The polypeptides of the gene variants may be expressed in prokaryotic cells by using suitable prokaryotic expression vectors. The cDNA fragments of GAK1 and GAK2 genes encoding the amino acid coding sequence may be PCR amplified with restriction enzyme digestion sites incorporated in the 5' and 3' ends, respectively. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)). Recombinant protein synthesis may be stimulated by the addition of 0.4 mM isopropylthiogalactoside (IPTG) for 3 hours. The bacterially-expressed proteins may be purified.

The polypeptides of GAK1 and GAK2 may be expressed in animal cells by using eukaryotic expression vectors. Cells may be maintained in Dulbecco's modified Eagle's medium (DMEM) supplemented with 10% fetal bovine serum (FBS; Gibco BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of $5\times10^4$ cells per well. Transfections may be carried out using Lipofectamine Plus transfection reagent according to the manufacturer's instructions (Gibco BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (GAK1 and GAK2) may be generated using hybridoma technique according to the conventional methods (de StGroth and Scheidegger, (1980) J Immunol Methods 35:1–21; Cote et al. (1983) Proc Natl Acad Sci U S A 80: 2026–30; and Kozbor et al. (1985) J Immunol Methods 81:31–42).

According to the present invention, the presence of the polypeptides of the gene variants in samples of normal lung and lung cancers may be determined by, but is not limited to, Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 hour at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human lung (normal and large cell lung cancer) cDNA clones were compiled and served as EST databases. Sequence comparisons against the nonredundant nucleotide and protein databases were performed using BLASTN and BLASTX programs (Altschul et al., (1997) Nucleic Acids Res. 25: 3389–3402; Gish and States, (1993) Nat Genet 3:266–272), at the National Center for Biotechnology Information (NCBI) with a significance cutoff of $p<10^{-10}$. ESTs representing putative GAK encoding gene were identified during the course of EST generation.

Isolation of cDNA Clones

Two cDNA clones exhibiting EST sequences similar to the GAK gene were isolated from the lung cDNA libraries and named GAK1 and GAK2. The inserts of these clones were subsequently excised in vivo from the λZAP Express vector using the ExAssist/XLOLR helper phage system (Stratagene). Phagemid particles were excised by coinfecting XL1-BLUE MRF' cells with ExAssist helper phage. The excised pBluescript phagemids were used to infect *E. coli* XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and the DNA was purified using a Qiagen plasmid purification kit.

Full Length Nucleotide Sequencing and Database Comparisons

Phagemid DNA was sequenced using the Epicentre#SE9101LC SequiTherm EXCEL™II DNA Sequencing Kit for 4200S-2 Global NEW IR$^2$ DNA sequencing system (LI-COR). Using the primer-walking approach, full-length sequence was determined. Nucleotide and protein searches were performed using BLAST against the non-redundant database of NCBI.

In Silico Tissue Distribution Analysis

The coding sequence for each cDNA clones was searched against the dbEST sequence database (Boguski et al., (1993) Nat Genet. 4: 332–3) using the BLAST algorithm at the NCBI website. ESTs derived from each tissue were used as a source of information for transcript tissue expression analysis. Tissue distribution for each isolated cDNA clone was determined by ESTs matching that particular sequence variants (insertions or deletions) with a significance cutoff of $p<10^{-10}$.

REFERENCES

Altschul et al., Gapped BLAST and PSI-BLAST: a new generation of protein database search programs, Nucleic Acids Res, 25: 3389–3402, (1997).

Ausubel et al., Current protocols in Molecular Biology, John Wiley & Sons, New York N.Y., ch. 9, 13, and 16, (1995).

Bates et al., Characterisation of human cyclin G1 and G2: DNA damage inducible genes. Oncogene, 13:1103–9, (1996).

Boguski et al., dbEST—database for "expressed sequence tags". Nat Genet. 4: 332–3, (1993).

Camey, D. N. The biology of lung cancer. Curr. Opin. Oncol. 4: 292–8, (1992a).

Camey, D. N. Biology of small-cell lung cancer. Lancet 339: 843–6, (1992b).

Cote et al., Generation of human monoclonal antibodies reactive with cellular antigens, Proc Natl Acad Sci U S A 80: 2026–30 (1983).

de StGroth and Scheidegger, Production of monoclonal antibodies: strategy and tactics, J Immunol Methods 35:1–21, (1980).

Earley et al., Insight into the pathophysiology of restless legs syndrome. J Neurosci Res, 62:623–8, (2000).

Gish and States, Identification of protein coding regions by database similarity search, Nat Genet, 3:266–272, (1993).

Home et al., Cyclin G1 and cyclin G2 comprise a new family of cyclins with contrasting tissue-specific and cell cycle-regulated expression. J Biol Chem, 271:6050–61, (1996).

Hunter and Pines, Cyclins and cancer. Cell, 66:1071–4, (1991).

Ihde and Minna, Non-small cell lung cancer. Part II: Treatment. Curr. Probl. Cancer 15: 105–54, (1991).

Jiang et al., Amplification and expression of the human cyclin D gene in esophageal cancer. Cancer Res, 52:2980–3, (1992).

Kanaoka et al., GAK: a cyclin G associated kinase contains a tensin/auxilin-like domain. FEBS Lett, 402:73–80, (1997).

Keyomarsi and Pardee, Redundant cyclin overexpression and gene amplification in breast cancer cells. Proc Natl Acad Sci U S A 90:1112–6, (1993).

Kimura et al., Structure, expression, and chromosomal localization of human GAK. Genomics 44:179–87, (1997).

Kohno et al., p53 mutation and allelic loss of chromosome 3p, 9p of preneoplastic lesions in patients with nonsmall cell lung carcinoma, Cancer 85: 341–7, (1999).

Kozak, An analysis of 5'-noncoding sequences from 699 vertebrate messenger RNAs. Nucleic Acids Res, 15: 8125–48, (1987).

Kozak, An analysis of vertebrate mRNA sequences: intimations of translational control, J Cell Biol, 115: 887–903, (1991).

Kozbor et al., Specific immunoglobulin production and enhanced tumorigenicity following ascites growth of human hybridomas, J Immunol Methods, 81:31–42 (1985).

Lammie et al., D11S287, a putative oncogene on chromosome 11q13, is amplified and expressed in squamous cell and mammary carcinomas and linked to BCL-1. Oncogene, 6:439–44, (1991).

Liu et al., Silent mutation induces exon skipping of fibrillin-1 gene in Marfan syndrome. Nat Genet 16:328–9, (1997).

Lukas et al., Alternative and aberrant messenger RNA splicing of the mdm2 oncogene in invasive breast cancer. Cancer Res 61:3212–9, (2001).

Lundrigan and Kadner, Nucleotide sequence of the gene for the ferrienterochelin receptor FepA in *Escherichia coli*. Homology among outer membrane receptors that interact with TonB. J Biol Chem 261:10797–801, (1986).

Michelland et al., Comparison of chromosomal imbalances in neuroendocrine and non-small-cell lung carcinomas. Cancer Genet Cytogenet, 114:22–30, (1999).

Ogunnariwo and Schryvers, Characterization of a novel transferrin receptor in bovine strains of *Pasteurella multocida*. J Bacteriol, 183:890–6, (2001).

Okamoto and Beach, Cyclin G is a transcriptional target of the p53 tumor suppressor protein. EMBO J, 13:4816–22, (1994).

Reimer et al., CL, Altered regulation of cyclin G in human breast cancer and its specific localization at replication foci in response to DNA damage in p53+/+cells. J Biol Chem, 274:11022–9, (1999).

Roberge et al., A strategy for a convergent synthesis of N-linked glycopeptides on a solid support. Science 269:202–4, (1995).

Sambrook, J. Cold Spring Harbor Press, Plainview N.Y., ch. 4, 8, and 16–17.

Schramm et al., Nucleotide sequence of the colicin B activity gene cba: consensus pentapeptide among TonB-dependent colicins and receptors. J Bacteriol, 169:3350–7, (1987).

Sethi, Science, medicine, and the future. Lung cancer, BMJ, 314: 652–655, (1997)

Siffert et al., Association of a human G-protein beta3 subunit variant with hypertension. Nat Genet, 18:45–8, (1998).

Simpson A. J. G. EST Accession No. B1026835

Skotzko et al., Retroviral vector-mediated gene transfer of antisense cyclin G1 (CYCG1) inhibits proliferation of human osteogenic sarcoma cells. Cancer Res, 55:5493–8, (1995).

Smith et al., The p53-regulated cyclin G gene promotes cell growth: p53 downstream effectors cyclin G and Gadd45 exert different effects on cisplatin chemosensitivity. Exp Cell Res, 230:61–8, (1997).

Smyth et al., The impact of chemotherapy on small cell carcinoma of the bronchus. Q J Med, 61: 969–76, (1986).

Stallings-Mann et al., Alternative splicing of exon 3 of the human growth hormone receptor is the result of an unusual genetic polymorphism. Proc Natl Acad Sci U S A 93:12394–9, (1996).

Strausberg, R. EST Accession No. BC008668, BE619037, BG333001, BG746688, BG821224

Tuomainen et al., Association between body iron stores and the risk of acute myocardial infarction in men. Circulation, 97:1461–6, (1998).

Weinberg E D, Iron depletion: a defense against intracellular infection and neoplasia. Life Sci, 50:1289–97, (1992).

Weinberg E D, The role of iron in cancer. Eur J Cancer Prev, 5:19–36, (1996).

Weinberg E D, Iron, infection and sudden infant death. Med Hypotheses, 56:731–4, (2001).

Weinstat-Saslow et al., Overexpression of cyclin D mRNA distinguishes invasive and in situ breast carcinomas from non-malignant lesions. Nat Med, 1:1257–60, (1995).

What is claimed is:

1. An isolated polypeptide which is a variant of cyclin G-associated protein kinase consisting of the amino acid sequence of SEQ ID NO: 2 or 4.

2. An isolated polypeptide consisting of the amino acid sequence of SEQ ID NO: 2.

3. An isolated polypeptide consisting of the amino acid sequence of SEQ ID NO: 4.

4. A method of detecting the polypeptide of claim 1 in a patient's protein sample, wherein the method comprises contacting an antibody specifically binding polypeptide of claim 1 with the sample and detecting whether an antibody-polypeptide complex is formed.

5. The method of claim 4, wherein the patient suffers from large cell lung cancer.

6. The method of claim 4 further comprising the step of determining the amount of the antibody-polypeptide complex.

* * * * *

SEQUENCE LISTING

```
<160> NUMBER OF SEQ ID NOS: 4

<210> SEQ ID NO 1
<211> LENGTH: 4308
<212> TYPE: DNA
<213> ORGANISM: Homo sapiens
<220> FEATURE:
<221> NAME/KEY: CDS
<222> LOCATION: (11)..(3910)
<223> OTHER INFORMATION:

<400> SEQUENCE: 1

agccaccgcc atg tcg ctg ctg cag tct gcg ctc gac ttc ttg gcg ggt        49
           Met Ser Leu Leu Gln Ser Ala Leu Asp Phe Leu Ala Gly
           1               5                   10

cca ggc tcc ctg ggc ggt gct tcc ggc cgc gac cag agt gac ttc gtg       97
Pro Gly Ser Leu Gly Gly Ala Ser Gly Arg Asp Gln Ser Asp Phe Val
    15                  20                  25

ggg cag acg gtg gaa ctg ggc gag ctg cgg ctg cgg gtg cgg cgg gtc      145
Gly Gln Thr Val Glu Leu Gly Glu Leu Arg Leu Arg Val Arg Arg Val
30                  35                  40                  45

ctg gcc gaa gga ggg ttt gca ttt gtg tat gaa gct caa gat gtg ggg      193
Leu Ala Glu Gly Gly Phe Ala Phe Val Tyr Glu Ala Gln Asp Val Gly
                50                  55                  60

agt ggc aga gag tat gca tta aag agg cta tta tcc aat gaa gag gaa      241
```

-continued

```
Ser Gly Arg Glu Tyr Ala Leu Lys Arg Leu Leu Ser Asn Glu Glu
            65                  70                  75

aag aac aga gcc atc att caa gaa gtt tgc ttc atg aaa aag ctt tcc      289
Lys Asn Arg Ala Ile Ile Gln Glu Val Cys Phe Met Lys Lys Leu Ser
        80                  85                  90

ggc cac ccg aac att gtc cag ttt tgt tct gca gcg tct ata gga aaa      337
Gly His Pro Asn Ile Val Gln Phe Cys Ser Ala Ala Ser Ile Gly Lys
    95                  100                 105

gag gag tca gac acg ggg cag gct gag ttc ctc ttg ctc aca gag ctc      385
Glu Glu Ser Asp Thr Gly Gln Ala Glu Phe Leu Leu Leu Thr Glu Leu
110                 115                 120                 125

tgt aaa ggg cag ctg gtg gaa ttt ttg aag aaa atg gaa tct cga ggc      433
Cys Lys Gly Gln Leu Val Glu Phe Leu Lys Lys Met Glu Ser Arg Gly
                130                 135                 140

ccc ctt tcg tgc gac acg gtt ctg aag atc ttc tac cag acg tgc cgc      481
Pro Leu Ser Cys Asp Thr Val Leu Lys Ile Phe Tyr Gln Thr Cys Arg
            145                 150                 155

gcc gtg cag cac atg cac cgg cag aag ccg ccc atc atc cac agg gac      529
Ala Val Gln His Met His Arg Gln Lys Pro Pro Ile Ile His Arg Asp
        160                 165                 170

ctc aag gtt gag aac ttg ttg ctt agt aac caa ggg acc att aag ctg      577
Leu Lys Val Glu Asn Leu Leu Leu Ser Asn Gln Gly Thr Ile Lys Leu
    175                 180                 185

tgt gac ttt ggc agt gcc acg acc atc tcg cac tac cct gac tac agc      625
Cys Asp Phe Gly Ser Ala Thr Thr Ile Ser His Tyr Pro Asp Tyr Ser
190                 195                 200                 205

tgg agc gcc cag agg cga gcc ctg gtg gag gaa gag atc acg agg aat      673
Trp Ser Ala Gln Arg Arg Ala Leu Val Glu Glu Glu Ile Thr Arg Asn
                210                 215                 220

aca aca cca atg tat aga aca cca gaa atc ata gac ttg tat tcc aac      721
Thr Thr Pro Met Tyr Arg Thr Pro Glu Ile Ile Asp Leu Tyr Ser Asn
            225                 230                 235

ttc ccg atc ggc gag aag cag gat atc tgg gcc ctg ggc tgc atc ttg      769
Phe Pro Ile Gly Glu Lys Gln Asp Ile Trp Ala Leu Gly Cys Ile Leu
        240                 245                 250

tac ctg ctg tgc ttc cgg cag cac cct ttt gag gat gga gcg aaa ctt      817
Tyr Leu Leu Cys Phe Arg Gln His Pro Phe Glu Asp Gly Ala Lys Leu
    255                 260                 265

cga ata gtc aat ggg aag tac tcg atc ccc ccg cac gac acg cag tac      865
Arg Ile Val Asn Gly Lys Tyr Ser Ile Pro Pro His Asp Thr Gln Tyr
270                 275                 280                 285

acg gtc ttc cac agc ctc atc cgc gcc atg ctg cag gtg aac ccg gag      913
Thr Val Phe His Ser Leu Ile Arg Ala Met Leu Gln Val Asn Pro Glu
                290                 295                 300

gag cgg ctg tcc atc gcc gag gtg gtg cac cag ctg cag gag atc gcg      961
Glu Arg Leu Ser Ile Ala Glu Val Val His Gln Leu Gln Glu Ile Ala
            305                 310                 315

gcc gcc cgc aac gtg aac ccc aag tct ccc atc aca gag ctc ctg gag     1009
Ala Ala Arg Asn Val Asn Pro Lys Ser Pro Ile Thr Glu Leu Leu Glu
        320                 325                 330

cag aat gga ggc tac ggg agc gcc aca ctg tcc cga ggg cca ccc cct     1057
Gln Asn Gly Gly Tyr Gly Ser Ala Thr Leu Ser Arg Gly Pro Pro Pro
    335                 340                 345

ccc gtg ggc ccc gct ggc agt ggc tac agt gga ggc ctg gcg ctg gcg     1105
Pro Val Gly Pro Ala Gly Ser Gly Tyr Ser Gly Gly Leu Ala Leu Ala
350                 355                 360                 365

gag tac gac cag ccg tat ggc ggc ttc ctg gac att ctg cgg ggt ggg     1153
Glu Tyr Asp Gln Pro Tyr Gly Gly Phe Leu Asp Ile Leu Arg Gly Gly
                370                 375                 380
```

-continued

```
aca gag cgg ctc ttc acc aac ctc aag gac acc tcc tcc aag gtc atc      1201
Thr Glu Arg Leu Phe Thr Asn Leu Lys Asp Thr Ser Ser Lys Val Ile
            385                 390                 395

cag tcc gtc gct aat tat gca aag ggt gac ctg gac ata tct tac atc      1249
Gln Ser Val Ala Asn Tyr Ala Lys Gly Asp Leu Asp Ile Ser Tyr Ile
        400                 405                 410

aca tcc aga att gca gtg atg tca ttc cca gca gaa ggt gtg gag tca      1297
Thr Ser Arg Ile Ala Val Met Ser Phe Pro Ala Glu Gly Val Glu Ser
    415                 420                 425

gcg ctc aaa aac aac atc gaa gat gtg cgg ttg ttc ctg gac tcc aag      1345
Ala Leu Lys Asn Asn Ile Glu Asp Val Arg Leu Phe Leu Asp Ser Lys
430                 435                 440                 445

cac cca ggg cac tat gcc gtc tac aac ctg tcc ccg agg acc tac cgg      1393
His Pro Gly His Tyr Ala Val Tyr Asn Leu Ser Pro Arg Thr Tyr Arg
                450                 455                 460

ccc tcc agg ttc cac aac cgg gtc tcc gag tgt ggc tgg gca gca cgg      1441
Pro Ser Arg Phe His Asn Arg Val Ser Glu Cys Gly Trp Ala Ala Arg
            465                 470                 475

cgg gcc cca cac ctg cac acc ctg tac aac atc tgc agg aac atg cac      1489
Arg Ala Pro His Leu His Thr Leu Tyr Asn Ile Cys Arg Asn Met His
        480                 485                 490

gcc tgg ctg cgg cag gac cac aag aac gtc tgc gtc gtg cac tgc atg      1537
Ala Trp Leu Arg Gln Asp His Lys Asn Val Cys Val Val His Cys Met
    495                 500                 505

gac ggg aga gcc gcg tct gct gtg gcc gtc tgc tcc ttc ctg tgc ttc      1585
Asp Gly Arg Ala Ala Ser Ala Val Ala Val Cys Ser Phe Leu Cys Phe
510                 515                 520                 525

tgc cgt ctc ttc agc acc gcg gag gcc gcc gtg tac atg ttc agc atg      1633
Cys Arg Leu Phe Ser Thr Ala Glu Ala Ala Val Tyr Met Phe Ser Met
                530                 535                 540

aag cgc tgc cca cca ggc atc tgg cca tcc cac aaa agg tac atc gag      1681
Lys Arg Cys Pro Pro Gly Ile Trp Pro Ser His Lys Arg Tyr Ile Glu
            545                 550                 555

tac atg tgt gac atg gtg gcg gag gag ccc atc aca ccc cac agc aag      1729
Tyr Met Cys Asp Met Val Ala Glu Glu Pro Ile Thr Pro His Ser Lys
        560                 565                 570

ccc atc ctg gtg agg gcc gtg gtc atg aca ccc gtg ccg ctg ttc agc      1777
Pro Ile Leu Val Arg Ala Val Val Met Thr Pro Val Pro Leu Phe Ser
    575                 580                 585

aag cag agg agc ggc tgc agg ccc ttc tgc gag gtc tac gtg ggg gac      1825
Lys Gln Arg Ser Gly Cys Arg Pro Phe Cys Glu Val Tyr Val Gly Asp
590                 595                 600                 605

gag cgt gtg gcc agc acc tcc cag gag tac gac aag atg cgg gac ttt      1873
Glu Arg Val Ala Ser Thr Ser Gln Glu Tyr Asp Lys Met Arg Asp Phe
                610                 615                 620

aag att gaa gat ggc aaa gcg gtg att ccc ctg ggc gtc acg gtg caa      1921
Lys Ile Glu Asp Gly Lys Ala Val Ile Pro Leu Gly Val Thr Val Gln
            625                 630                 635

gga gac gtg ctc atc gtc atc tat cac gcc cgg tcc act ctg ggc ggc      1969
Gly Asp Val Leu Ile Val Ile Tyr His Ala Arg Ser Thr Leu Gly Gly
        640                 645                 650

cgg ctg cag gcc aag atg gca tcc atg aag atg ttc cag att cag ttc      2017
Arg Leu Gln Ala Lys Met Ala Ser Met Lys Met Phe Gln Ile Gln Phe
    655                 660                 665

cac acg ggg ttt gtg cct cgg aac gcc acc act gtg aaa ttt gcc aag      2065
His Thr Gly Phe Val Pro Arg Asn Ala Thr Thr Val Lys Phe Ala Lys
670                 675                 680                 685

tat gac ctg gac gcg tgt gac att caa gaa aaa tac ccg gat tta ttt      2113
Tyr Asp Leu Asp Ala Cys Asp Ile Gln Glu Lys Tyr Pro Asp Leu Phe
                690                 695                 700
```

-continued

```
caa gtg aac ctg gaa gtg gag gtg gag ccc agg gac agg ccg agc cgg      2161
Gln Val Asn Leu Glu Val Glu Val Glu Pro Arg Asp Arg Pro Ser Arg
            705                 710                 715

gaa gcc cca cca tgg gag aac tcg agc atg agg ggg ctg aac ccc aaa      2209
Glu Ala Pro Pro Trp Glu Asn Ser Ser Met Arg Gly Leu Asn Pro Lys
        720                 725                 730

atc ctg ttt tcc agc cgg gag gag cag caa gac att ctg tct aag ttt      2257
Ile Leu Phe Ser Ser Arg Glu Glu Gln Gln Asp Ile Leu Ser Lys Phe
    735                 740                 745

ggg aag ccg gag ctt ccc cgg cag cct ggc tcc acg gct cag tat gat      2305
Gly Lys Pro Glu Leu Pro Arg Gln Pro Gly Ser Thr Ala Gln Tyr Asp
750                 755                 760                 765

gct ggg gca ggg tcc ccg gaa gcc gaa ccc aca gac tct gac tca ccg      2353
Ala Gly Ala Gly Ser Pro Glu Ala Glu Pro Thr Asp Ser Asp Ser Pro
            770                 775                 780

cca agc agc agc gcg gac gcc agt cgc ttc ctg cac acg ctg gac tgg      2401
Pro Ser Ser Ser Ala Asp Ala Ser Arg Phe Leu His Thr Leu Asp Trp
            785                 790                 795

cag gaa gag aag gag gca gag act ggt gca gaa aat gcc tct tcc aag      2449
Gln Glu Glu Lys Glu Ala Glu Thr Gly Ala Glu Asn Ala Ser Ser Lys
        800                 805                 810

gag agc gag tct gcc ctg atg gag gac aga gac gag agt gag gtg tca      2497
Glu Ser Glu Ser Ala Leu Met Glu Asp Arg Asp Glu Ser Glu Val Ser
    815                 820                 825

gat gaa ggg gga tcc ccg atc tcc agc gag ggc cag gaa ccc agg gcc      2545
Asp Glu Gly Gly Ser Pro Ile Ser Ser Glu Gly Gln Glu Pro Arg Ala
830                 835                 840                 845

gac cca gag ccc ccc ggc ctg gca gca ggg ctg gtg cag cag gac ttg      2593
Asp Pro Glu Pro Pro Gly Leu Ala Ala Gly Leu Val Gln Gln Asp Leu
            850                 855                 860

gtt ttt gag gtg gag aca ccg gct gtg ctg cca gag cct gtg cca cag      2641
Val Phe Glu Val Glu Thr Pro Ala Val Leu Pro Glu Pro Val Pro Gln
            865                 870                 875

gaa gac ggg gtc gac ctc ctg ggc ctg cac tcc gag gtg ggc gca ggg      2689
Glu Asp Gly Val Asp Leu Leu Gly Leu His Ser Glu Val Gly Ala Gly
        880                 885                 890

cca gct gta ccc ccg cag gcc tgc aag gcc ccc tcc agc aac acc gac      2737
Pro Ala Val Pro Pro Gln Ala Cys Lys Ala Pro Ser Ser Asn Thr Asp
    895                 900                 905

ctg ctc agc tgc ctc ctt ggg ccc cct gag gcc gcc tcc cag ggg ccc      2785
Leu Leu Ser Cys Leu Leu Gly Pro Pro Glu Ala Ala Ser Gln Gly Pro
910                 915                 920                 925

ccg gag gat ctg ctc agc gag gac ccg ctg ctc ctg gca agc ccg gcc      2833
Pro Glu Asp Leu Leu Ser Glu Asp Pro Leu Leu Leu Ala Ser Pro Ala
            930                 935                 940

cct ccc ctg agc gtg cag agc acc cca aga gga ggg ccc cct gcc gct      2881
Pro Pro Leu Ser Val Gln Ser Thr Pro Arg Gly Gly Pro Pro Ala Ala
            945                 950                 955

ggc aac aac tcc cag ccc tgc tcc aat cct gat ctc ttc ggc gaa ttt      2929
Gly Asn Asn Ser Gln Pro Cys Ser Asn Pro Asp Leu Phe Gly Glu Phe
        960                 965                 970

ctc aat tcg gac tct gtg acc gtc cca cca tcc ttc ccg tct gcc cac      2977
Leu Asn Ser Asp Ser Val Thr Val Pro Pro Ser Phe Pro Ser Ala His
    975                 980                 985

agc gct ccg ccc cca tcc tgc agc gcc gac ttc  ctg cac ctg ggg gat     3025
Ser Ala Pro Pro Pro Ser Cys Ser Ala Asp Phe  Leu His Leu Gly Asp
990                 995                 1000                 1005

ctg cca gga gag ccc  agc aag atg aca gcc  tcg tcc agc aac cca        3070
Leu Pro Gly Glu Pro  Ser Lys Met Thr Ala  Ser Ser Ser Asn Pro
```

-continued

```
                1010                1015                1020

gac ctg ctg gga gga  tgg gct gcc tgg acc  gag act gca gcg tcg      3115
Asp Leu Leu Gly Gly  Trp Ala Ala Trp Thr  Glu Thr Ala Ala Ser
                1025                1030                1035

gca gtg gcc ccc acg  cca gcc aca gaa ggc  ccc ctc ttc tct cct      3160
Ala Val Ala Pro Thr  Pro Ala Thr Glu Gly  Pro Leu Phe Ser Pro
                1040                1045                1050

gga ggt cag ccg gcc  cct tgt ggc tct cag  gcc agc tgg acc aag      3205
Gly Gly Gln Pro Ala  Pro Cys Gly Ser Gln  Ala Ser Trp Thr Lys
                1055                1060                1065

tct cag aac ccg gac  cca ttt gct gac ctt  ggc gac ctc agc tcc      3250
Ser Gln Asn Pro Asp  Pro Phe Ala Asp Leu  Gly Asp Leu Ser Ser
                1070                1075                1080

ggc ctc caa ggc tca  cca gct gga ttt cct  cct ggg ggc ttc att      3295
Gly Leu Gln Gly Ser  Pro Ala Gly Phe Pro  Pro Gly Gly Phe Ile
                1085                1090                1095

ccc aaa acg gcc acc  acg gcc aaa ggc agc  agc tcc tgg cag aca      3340
Pro Lys Thr Ala Thr  Thr Ala Lys Gly Ser  Ser Ser Trp Gln Thr
                1100                1105                1110

agt cgg ccg cca gcc  cag ggc gcc tca tgg  ccc cct cag gcc aag      3385
Ser Arg Pro Pro Ala  Gln Gly Ala Ser Trp  Pro Pro Gln Ala Lys
                1115                1120                1125

ccg ccc ccc aaa gcc  tgc aca cag cca agg  cct aac tat gcc tcg      3430
Pro Pro Pro Lys Ala  Cys Thr Gln Pro Arg  Pro Asn Tyr Ala Ser
                1130                1135                1140

aac ttc agt gtg atc  ggg gcg cgg gag gag  cgg ggg gtc cgc gca      3475
Asn Phe Ser Val Ile  Gly Ala Arg Glu Glu  Arg Gly Val Arg Ala
                1145                1150                1155

ccc agc ttt gct caa  aag cca aaa gtc tct  gag aac gac ttt gaa      3520
Pro Ser Phe Ala Gln  Lys Pro Lys Val Ser  Glu Asn Asp Phe Glu
                1160                1165                1170

gat ctg ttg tcc aat  caa ggc ttc tcc tcc  agg tct gac aag aaa      3565
Asp Leu Leu Ser Asn  Gln Gly Phe Ser Ser  Arg Ser Asp Lys Lys
                1175                1180                1185

ggg cca aag acc att  gca gag atg agg aag  cag gac ctg gct aaa      3610
Gly Pro Lys Thr Ile  Ala Glu Met Arg Lys  Gln Asp Leu Ala Lys
                1190                1195                1200

gac acg gac cca ctc  aag ctg aag ctc ctg  gac tgg att gag ggc      3655
Asp Thr Asp Pro Leu  Lys Leu Lys Leu Leu  Asp Trp Ile Glu Gly
                1205                1210                1215

aag gag cgg aac atc  cgg gcc ctg ctg tcc  acg ctg cac aca gtg      3700
Lys Glu Arg Asn Ile  Arg Ala Leu Leu Ser  Thr Leu His Thr Val
                1220                1225                1230

ctg tgg gac ggg gag  agc cgc tgg acg ccc  gtg ggc atg gcc gac      3745
Leu Trp Asp Gly Glu  Ser Arg Trp Thr Pro  Val Gly Met Ala Asp
                1235                1240                1245

ctg gtg gct ccg gag  caa gtg aag aag cac  tat cgc cgc gcg gtg      3790
Leu Val Ala Pro Glu  Gln Val Lys Lys His  Tyr Arg Arg Ala Val
                1250                1255                1260

ctg gcc gtg cac ccc  gac aag gct gcg ggg  cag ccg tac gag cag      3835
Leu Ala Val His Pro  Asp Lys Ala Ala Gly  Gln Pro Tyr Glu Gln
                1265                1270                1275

cac gcc aag atg atc  ttc atg gag ctg aat  gac gcc tgg tcg gag      3880
His Ala Lys Met Ile  Phe Met Glu Leu Asn  Asp Ala Trp Ser Glu
                1280                1285                1290

ttt gag aac cag ggc  tcc cgg ccc ctc ttc  tgaggccgca gtggtggtgg    3930
Phe Glu Asn Gln Gly  Ser Arg Pro Leu Phe
                1295                1300

ctgcgcacac agctccacag gttgggagcc gtcgtgggac ctgggtcccc accgtgagga  3990
```

```
ccccgtgggc gacagcaggt gtggccaggg tggggctccg agccccgggt caccgcccgc   4050

ccagcgttcc aggcacatga agagaaagca ttccaaagcc tctgattgtt gtttcctttt   4110

tctcctcccg aaggaacagc tgattcatgc tcctcccgca attgtcacgt ctgtgattta   4170

tttggtgttt cgggcgtggc ctctggagcc ccggcacgtg gtgggccacg ctgctggcgc   4230

tcatgggccc tggtgtttgc accgcacttt gtaatcagtc ccgtggttgt ctgtacagaa   4290

ttaaactatt ttccgatg                                                 4308


<210> SEQ ID NO 2
<211> LENGTH: 1300
<212> TYPE: PRT
<213> ORGANISM: Homo sapiens

<400> SEQUENCE: 2

Met Ser Leu Leu Gln Ser Ala Leu Asp Phe Leu Ala Gly Pro Gly Ser
1               5                   10                  15

Leu Gly Gly Ala Ser Gly Arg Asp Gln Ser Asp Phe Val Gly Gln Thr
            20                  25                  30

Val Glu Leu Gly Glu Leu Arg Leu Arg Val Arg Arg Val Leu Ala Glu
        35                  40                  45

Gly Gly Phe Ala Phe Val Tyr Glu Ala Gln Asp Val Gly Ser Gly Arg
    50                  55                  60

Glu Tyr Ala Leu Lys Arg Leu Leu Ser Asn Glu Glu Glu Lys Asn Arg
65                  70                  75                  80

Ala Ile Ile Gln Glu Val Cys Phe Met Lys Lys Leu Ser Gly His Pro
                85                  90                  95

Asn Ile Val Gln Phe Cys Ser Ala Ala Ser Ile Gly Lys Glu Glu Ser
            100                 105                 110

Asp Thr Gly Gln Ala Glu Phe Leu Leu Leu Thr Glu Leu Cys Lys Gly
        115                 120                 125

Gln Leu Val Glu Phe Leu Lys Lys Met Glu Ser Arg Gly Pro Leu Ser
    130                 135                 140

Cys Asp Thr Val Leu Lys Ile Phe Tyr Gln Thr Cys Arg Ala Val Gln
145                 150                 155                 160

His Met His Arg Gln Lys Pro Pro Ile Ile His Arg Asp Leu Lys Val
                165                 170                 175

Glu Asn Leu Leu Leu Ser Asn Gln Gly Thr Ile Lys Leu Cys Asp Phe
            180                 185                 190

Gly Ser Ala Thr Thr Ile Ser His Tyr Pro Asp Tyr Ser Trp Ser Ala
        195                 200                 205

Gln Arg Arg Ala Leu Val Glu Glu Glu Ile Thr Arg Asn Thr Thr Pro
    210                 215                 220

Met Tyr Arg Thr Pro Glu Ile Ile Asp Leu Tyr Ser Asn Phe Pro Ile
225                 230                 235                 240

Gly Glu Lys Gln Asp Ile Trp Ala Leu Gly Cys Ile Leu Tyr Leu Leu
                245                 250                 255

Cys Phe Arg Gln His Pro Phe Glu Asp Gly Ala Lys Leu Arg Ile Val
            260                 265                 270

Asn Gly Lys Tyr Ser Ile Pro Pro His Asp Thr Gln Tyr Thr Val Phe
        275                 280                 285

His Ser Leu Ile Arg Ala Met Leu Gln Val Asn Pro Glu Glu Arg Leu
    290                 295                 300

Ser Ile Ala Glu Val Val His Gln Leu Gln Glu Ile Ala Ala Ala Arg
```

-continued

```
305                 310                 315                 320

Asn Val Asn Pro Lys Ser Pro Ile Thr Glu Leu Leu Glu Gln Asn Gly
                325                 330                 335

Gly Tyr Gly Ser Ala Thr Leu Ser Arg Gly Pro Pro Pro Val Gly
            340                 345                 350

Pro Ala Gly Ser Gly Tyr Ser Gly Gly Leu Ala Leu Ala Glu Tyr Asp
        355                 360                 365

Gln Pro Tyr Gly Gly Phe Leu Asp Ile Leu Arg Gly Gly Thr Glu Arg
    370                 375                 380

Leu Phe Thr Asn Leu Lys Asp Thr Ser Ser Lys Val Ile Gln Ser Val
385                 390                 395                 400

Ala Asn Tyr Ala Lys Gly Asp Leu Asp Ile Ser Tyr Ile Thr Ser Arg
                405                 410                 415

Ile Ala Val Met Ser Phe Pro Ala Glu Gly Val Glu Ser Ala Leu Lys
            420                 425                 430

Asn Asn Ile Glu Asp Val Arg Leu Phe Leu Asp Ser Lys His Pro Gly
        435                 440                 445

His Tyr Ala Val Tyr Asn Leu Ser Pro Arg Thr Tyr Arg Pro Ser Arg
    450                 455                 460

Phe His Asn Arg Val Ser Glu Cys Gly Trp Ala Ala Arg Arg Ala Pro
465                 470                 475                 480

His Leu His Thr Leu Tyr Asn Ile Cys Arg Asn Met His Ala Trp Leu
                485                 490                 495

Arg Gln Asp His Lys Asn Val Cys Val Val His Cys Met Asp Gly Arg
            500                 505                 510

Ala Ala Ser Ala Val Ala Val Cys Ser Phe Leu Cys Phe Cys Arg Leu
        515                 520                 525

Phe Ser Thr Ala Glu Ala Ala Val Tyr Met Phe Ser Met Lys Arg Cys
    530                 535                 540

Pro Pro Gly Ile Trp Pro Ser His Lys Arg Tyr Ile Glu Tyr Met Cys
545                 550                 555                 560

Asp Met Val Ala Glu Glu Pro Ile Thr Pro His Ser Lys Pro Ile Leu
                565                 570                 575

Val Arg Ala Val Val Met Thr Pro Val Pro Leu Phe Ser Lys Gln Arg
            580                 585                 590

Ser Gly Cys Arg Pro Phe Cys Glu Val Tyr Val Gly Asp Glu Arg Val
        595                 600                 605

Ala Ser Thr Ser Gln Glu Tyr Asp Lys Met Arg Asp Phe Lys Ile Glu
    610                 615                 620

Asp Gly Lys Ala Val Ile Pro Leu Gly Val Thr Val Gln Gly Asp Val
625                 630                 635                 640

Leu Ile Val Ile Tyr His Ala Arg Ser Thr Leu Gly Gly Arg Leu Gln
                645                 650                 655

Ala Lys Met Ala Ser Met Lys Met Phe Gln Ile Gln Phe His Thr Gly
            660                 665                 670

Phe Val Pro Arg Asn Ala Thr Thr Val Lys Phe Ala Lys Tyr Asp Leu
        675                 680                 685

Asp Ala Cys Asp Ile Gln Glu Lys Tyr Pro Asp Leu Phe Gln Val Asn
    690                 695                 700

Leu Glu Val Glu Val Glu Pro Arg Asp Arg Pro Ser Arg Glu Ala Pro
705                 710                 715                 720

Pro Trp Glu Asn Ser Ser Met Arg Gly Leu Asn Pro Lys Ile Leu Phe
                725                 730                 735
```

-continued

```
Ser Ser Arg Glu Glu Gln Gln Asp Ile Leu Ser Lys Phe Gly Lys Pro
        740                 745                 750

Glu Leu Pro Arg Gln Pro Gly Ser Thr Ala Gln Tyr Asp Ala Gly Ala
    755                 760                 765

Gly Ser Pro Glu Ala Glu Pro Thr Asp Ser Asp Ser Pro Pro Ser Ser
    770                 775                 780

Ser Ala Asp Ala Ser Arg Phe Leu His Thr Leu Asp Trp Gln Glu Glu
785                 790                 795                 800

Lys Glu Ala Glu Thr Gly Ala Glu Asn Ala Ser Ser Lys Glu Ser Glu
                805                 810                 815

Ser Ala Leu Met Glu Asp Arg Asp Glu Ser Glu Val Ser Asp Glu Gly
        820                 825                 830

Gly Ser Pro Ile Ser Ser Glu Gly Gln Glu Pro Arg Ala Asp Pro Glu
    835                 840                 845

Pro Pro Gly Leu Ala Ala Gly Leu Val Gln Gln Asp Leu Val Phe Glu
    850                 855                 860

Val Glu Thr Pro Ala Val Leu Pro Glu Pro Val Pro Gln Glu Asp Gly
865                 870                 875                 880

Val Asp Leu Leu Gly Leu His Ser Glu Val Gly Ala Gly Pro Ala Val
                885                 890                 895

Pro Pro Gln Ala Cys Lys Ala Pro Ser Ser Asn Thr Asp Leu Leu Ser
        900                 905                 910

Cys Leu Leu Gly Pro Pro Glu Ala Ala Ser Gln Gly Pro Pro Glu Asp
    915                 920                 925

Leu Leu Ser Glu Asp Pro Leu Leu Leu Ala Ser Pro Ala Pro Pro Leu
    930                 935                 940

Ser Val Gln Ser Thr Pro Arg Gly Gly Pro Pro Ala Ala Gly Asn Asn
945                 950                 955                 960

Ser Gln Pro Cys Ser Asn Pro Asp Leu Phe Gly Glu Phe Leu Asn Ser
                965                 970                 975

Asp Ser Val Thr Val Pro Pro Ser Phe Pro Ser Ala His Ser Ala Pro
        980                 985                 990

Pro Pro Ser Cys Ser Ala Asp Phe  Leu His Leu Gly Asp  Leu Pro Gly
    995                 1000                1005

Glu Pro  Ser Lys Met Thr Ala  Ser Ser Ser Asn Pro  Asp Leu Leu
    1010                1015                1020

Gly Gly  Trp Ala Ala Trp Thr  Glu Thr Ala Ala Ser  Ala Val Ala
    1025                1030                1035

Pro Thr  Pro Ala Thr Glu Gly  Pro Leu Phe Ser Pro  Gly Gly Gln
    1040                1045                1050

Pro Ala  Pro Cys Gly Ser Gln  Ala Ser Trp Thr Lys  Ser Gln Asn
    1055                1060                1065

Pro Asp  Pro Phe Ala Asp Leu  Gly Asp Leu Ser Ser  Gly Leu Gln
    1070                1075                1080

Gly Ser  Pro Ala Gly Phe Pro  Pro Gly Gly Phe Ile  Pro Lys Thr
    1085                1090                1095

Ala Thr  Thr Ala Lys Gly Ser  Ser Ser Trp Gln Thr  Ser Arg Pro
    1100                1105                1110

Pro Ala  Gln Gly Ala Ser Trp  Pro Pro Gln Ala Lys  Pro Pro Pro
    1115                1120                1125

Lys Ala  Cys Thr Gln Pro Arg  Pro Asn Tyr Ala Ser  Asn Phe Ser
    1130                1135                1140
```

-continued

```
Val Ile  Gly Ala Arg Glu Glu  Arg Gly Val Arg Ala  Pro Ser Phe
    1145                 1150                 1155

Ala Gln  Lys Pro Lys Val Ser  Glu Asn Asp Phe Glu  Asp Leu Leu
    1160                 1165                 1170

Ser Asn  Gln Gly Phe Ser Ser  Arg Ser Asp Lys Lys  Gly Pro Lys
    1175                 1180                 1185

Thr Ile  Ala Glu Met Arg Lys  Gln Asp Leu Ala Lys  Asp Thr Asp
    1190                 1195                 1200

Pro Leu  Lys Leu Lys Leu Leu  Asp Trp Ile Glu Gly  Lys Glu Arg
    1205                 1210                 1215

Asn Ile  Arg Ala Leu Leu Ser  Thr Leu His Thr Val  Leu Trp Asp
    1220                 1225                 1230

Gly Glu  Ser Arg Trp Thr Pro  Val Gly Met Ala Asp  Leu Val Ala
    1235                 1240                 1245

Pro Glu  Gln Val Lys Lys His  Tyr Arg Arg Ala Val  Leu Ala Val
    1250                 1255                 1260

His Pro  Asp Lys Ala Ala Gly  Gln Pro Tyr Glu Gln  His Ala Lys
    1265                 1270                 1275

Met Ile  Phe Met Glu Leu Asn  Asp Ala Trp Ser Glu  Phe Glu Asn
    1280                 1285                 1290

Gln Gly  Ser Arg Pro Leu Phe
    1295                 1300


<210> SEQ ID NO 3
<211> LENGTH: 1740
<212> TYPE: DNA
<213> ORGANISM: Homo sapiens
<220> FEATURE:
<221> NAME/KEY: CDS
<222> LOCATION: (95)..(1342)
<223> OTHER INFORMATION:

<400> SEQUENCE: 3

gggccggcgg ttgctgagct gacccggacg gcgagggagc gggagcccga gcccgaccac     60

tccggctgcc gcggggtgcg gcgcagccac cgcc atg tcg ctg ctg cag tct gcg    115
                                      Met Ser Leu Leu Gln Ser Ala
                                      1               5

ctc gac ttc ttg gcg ggt cca ggc tcc ctg ggc ggt gct tcc ggc cgc      163
Leu Asp Phe Leu Ala Gly Pro Gly Ser Leu Gly Gly Ala Ser Gly Arg
        10                  15                  20

gac cag agt gac ttc gtg ggg cag acg gtg gaa ctg ggc gag ctg cgg      211
Asp Gln Ser Asp Phe Val Gly Gln Thr Val Glu Leu Gly Glu Leu Arg
    25                  30                  35

ctg ctc ctg gca agc ccg gcc cct ccc ctg agc gtg cag agc acc cca      259
Leu Leu Leu Ala Ser Pro Ala Pro Pro Leu Ser Val Gln Ser Thr Pro
40                  45                  50                  55

aga gga ggg ccc cct gcc gct gct gac ccc ttt ggc ccg ctt ctg ccg      307
Arg Gly Gly Pro Pro Ala Ala Ala Asp Pro Phe Gly Pro Leu Leu Pro
                60                  65                  70

tct tca ggc aac aac tcc cag ccc tgc tcc aat cct gat ctc ttc ggc      355
Ser Ser Gly Asn Asn Ser Gln Pro Cys Ser Asn Pro Asp Leu Phe Gly
            75                  80                  85

gaa ttt ctc aat tcg gac tct gtg acc gtc cca cca tcc ttc ccg tct      403
Glu Phe Leu Asn Ser Asp Ser Val Thr Val Pro Pro Ser Phe Pro Ser
        90                  95                  100

gcc cac agc gct ccg ccc cca tcc tgc agc gcc gac ttc ctg cac ctg      451
Ala His Ser Ala Pro Pro Pro Ser Cys Ser Ala Asp Phe Leu His Leu
    105                 110                 115
```

-continued

```
ggg gat ctg cca gga gag ccc agc aag atg aca gcc tcg tcc agc aac      499
Gly Asp Leu Pro Gly Glu Pro Ser Lys Met Thr Ala Ser Ser Ser Asn
120                 125                 130                 135

cca gac ctg ctg gga gga tgg gct gcc tgg acc gag act gca gcg tcg      547
Pro Asp Leu Leu Gly Gly Trp Ala Ala Trp Thr Glu Thr Ala Ala Ser
                140                 145                 150

gca gtg gcc ccc acg cca gcc aca gaa ggc ccc ctc ttc tct cct gga      595
Ala Val Ala Pro Thr Pro Ala Thr Glu Gly Pro Leu Phe Ser Pro Gly
            155                 160                 165

ggt cag ccg gcc cct tgt ggc tct cag gcc agc tgg acc aag tct cag      643
Gly Gln Pro Ala Pro Cys Gly Ser Gln Ala Ser Trp Thr Lys Ser Gln
        170                 175                 180

aac ccg gac cca ttt gct gac ctt ggc gac ctc agc tcc ggc ctc caa      691
Asn Pro Asp Pro Phe Ala Asp Leu Gly Asp Leu Ser Ser Gly Leu Gln
    185                 190                 195

ggc tca cca gct gga ttt cct cct ggg ggc ttc att ccc aaa acg gcc      739
Gly Ser Pro Ala Gly Phe Pro Pro Gly Gly Phe Ile Pro Lys Thr Ala
200                 205                 210                 215

acc acg gcc aaa ggc agc agc tcc tgg cag aca agt cgg ccg cca gcc      787
Thr Thr Ala Lys Gly Ser Ser Ser Trp Gln Thr Ser Arg Pro Pro Ala
                220                 225                 230

cag ggc gcc tca tgg ccc cct cag gcc aag ccg ccc ccc aaa gcc tgc      835
Gln Gly Ala Ser Trp Pro Pro Gln Ala Lys Pro Pro Pro Lys Ala Cys
            235                 240                 245

aca cag cca agg cct aac tat gcc tcg aac ttc agt gtg atc ggg gcg      883
Thr Gln Pro Arg Pro Asn Tyr Ala Ser Asn Phe Ser Val Ile Gly Ala
        250                 255                 260

cgg gag gag cgg ggg gtc cgc gca ccc agc ttt gct caa aag cca aaa      931
Arg Glu Glu Arg Gly Val Arg Ala Pro Ser Phe Ala Gln Lys Pro Lys
    265                 270                 275

gtc tct gag aac gac ttt gaa gat ctg ttg tcc aat caa ggc ttc tcc      979
Val Ser Glu Asn Asp Phe Glu Asp Leu Leu Ser Asn Gln Gly Phe Ser
280                 285                 290                 295

tcc agg tct gac aag aaa ggg cca aag acc att gca gag atg agg aag     1027
Ser Arg Ser Asp Lys Lys Gly Pro Lys Thr Ile Ala Glu Met Arg Lys
                300                 305                 310

cag gac ctg gct aaa gac acg gac cca ctc aag ctg aag ctc ctg gac     1075
Gln Asp Leu Ala Lys Asp Thr Asp Pro Leu Lys Leu Lys Leu Leu Asp
            315                 320                 325

tgg att gag ggc aag gag cgg aac atc cgg gcc ctg ctg tcc acg ctg     1123
Trp Ile Glu Gly Lys Glu Arg Asn Ile Arg Ala Leu Leu Ser Thr Leu
        330                 335                 340

cac aca gtg ctg tgg gac ggg gag agc cgc tgg acg ccc gtg ggc atg     1171
His Thr Val Leu Trp Asp Gly Glu Ser Arg Trp Thr Pro Val Gly Met
    345                 350                 355

gcc gac ctg gtg gct ccg gag caa gtg aag aag cac tat cgc cgc gcg     1219
Ala Asp Leu Val Ala Pro Glu Gln Val Lys Lys His Tyr Arg Arg Ala
360                 365                 370                 375

gtg ctg gcc gtg cac ccc gac aag gct gcg ggg cag ccg tac gag cag     1267
Val Leu Ala Val His Pro Asp Lys Ala Ala Gly Gln Pro Tyr Glu Gln
                380                 385                 390

cac gcc aag atg atc ttc atg gag ctg aat gac gcc tgg tcg gag ttt     1315
His Ala Lys Met Ile Phe Met Glu Leu Asn Asp Ala Trp Ser Glu Phe
            395                 400                 405

gag aac cag ggc tcc cgg ccc ctc ttc tgaggccgca gtggtggtgg           1362
Glu Asn Gln Gly Ser Arg Pro Leu Phe
        410                 415

ctgcgcacac agctccacag gttgggagcc gtcgtgggac ctgggtcccc accgtgagga   1422

ccccgtgggc gacagcaggt gtggccaggg tggggctccg agccccgggt caccgcccgc   1482
```

-continued

```
ccagcgttcc aggcacatga agagaaagca ttccaaagcc tctgattgtt gtttcctttt   1542

tctcctcccg aaggaacagc tgattcatgc tcctcccgca attgtcacgt ctgtgattta   1602

tttggtgttt cgggcgtggc ctctggagcc ccggcacgtg gtgggccacg ctgctggcgc   1662

tcatgggccc tggtgtttgc accgcacttt gtaatcagtc ccgtggttgt ctgtacagaa   1722

ttaaactatt ttccgatg                                                 1740
```

```
<210> SEQ ID NO 4
<211> LENGTH: 416
<212> TYPE: PRT
<213> ORGANISM: Homo sapiens

<400> SEQUENCE: 4

Met Ser Leu Leu Gln Ser Ala Leu Asp Phe Leu Ala Gly Pro Gly Ser
1               5                   10                  15

Leu Gly Gly Ala Ser Gly Arg Asp Gln Ser Asp Phe Val Gly Gln Thr
            20                  25                  30

Val Glu Leu Gly Glu Leu Arg Leu Leu Leu Ala Ser Pro Ala Pro Pro
        35                  40                  45

Leu Ser Val Gln Ser Thr Pro Arg Gly Gly Pro Pro Ala Ala Ala Asp
    50                  55                  60

Pro Phe Gly Pro Leu Leu Pro Ser Ser Gly Asn Asn Ser Gln Pro Cys
65                  70                  75                  80

Ser Asn Pro Asp Leu Phe Gly Glu Phe Leu Asn Ser Asp Ser Val Thr
                85                  90                  95

Val Pro Pro Ser Phe Pro Ser Ala His Ser Ala Pro Pro Pro Ser Cys
            100                 105                 110

Ser Ala Asp Phe Leu His Leu Gly Asp Leu Pro Gly Glu Pro Ser Lys
        115                 120                 125

Met Thr Ala Ser Ser Ser Asn Pro Asp Leu Leu Gly Gly Trp Ala Ala
    130                 135                 140

Trp Thr Glu Thr Ala Ala Ser Ala Val Ala Pro Thr Pro Ala Thr Glu
145                 150                 155                 160

Gly Pro Leu Phe Ser Pro Gly Gly Gln Pro Ala Pro Cys Gly Ser Gln
                165                 170                 175

Ala Ser Trp Thr Lys Ser Gln Asn Pro Asp Pro Phe Ala Asp Leu Gly
            180                 185                 190

Asp Leu Ser Ser Gly Leu Gln Gly Ser Pro Ala Gly Phe Pro Pro Gly
        195                 200                 205

Gly Phe Ile Pro Lys Thr Ala Thr Thr Ala Lys Gly Ser Ser Ser Trp
    210                 215                 220

Gln Thr Ser Arg Pro Pro Ala Gln Gly Ala Ser Trp Pro Pro Gln Ala
225                 230                 235                 240

Lys Pro Pro Pro Lys Ala Cys Thr Gln Pro Arg Pro Asn Tyr Ala Ser
                245                 250                 255

Asn Phe Ser Val Ile Gly Ala Arg Glu Glu Arg Gly Val Arg Ala Pro
            260                 265                 270

Ser Phe Ala Gln Lys Pro Lys Val Ser Glu Asn Asp Phe Glu Asp Leu
        275                 280                 285

Leu Ser Asn Gln Gly Phe Ser Ser Arg Ser Asp Lys Lys Gly Pro Lys
    290                 295                 300

Thr Ile Ala Glu Met Arg Lys Gln Asp Leu Ala Lys Asp Thr Asp Pro
305                 310                 315                 320
```

-continued

```
Leu Lys Leu Lys Leu Leu Asp Trp Ile Glu Gly Lys Glu Arg Asn Ile
                325                 330                 335

Arg Ala Leu Leu Ser Thr Leu His Thr Val Leu Trp Asp Gly Glu Ser
            340                 345                 350

Arg Trp Thr Pro Val Gly Met Ala Asp Leu Val Ala Pro Glu Gln Val
        355                 360                 365

Lys Lys His Tyr Arg Arg Ala Val Leu Ala Val His Pro Asp Lys Ala
    370                 375                 380

Ala Gly Gln Pro Tyr Glu Gln His Ala Lys Met Ile Phe Met Glu Leu
385                 390                 395                 400

Asn Asp Ala Trp Ser Glu Phe Glu Asn Gln Gly Ser Arg Pro Leu Phe
                405                 410                 415
```